(12) United States Patent
Kolczewski et al.

(10) Patent No.: US 7,923,561 B2
(45) Date of Patent: *Apr. 12, 2011

(54) QUINOLINES

(75) Inventors: Sabine Kolczewski, Loerrach (DE); Claus Riemer, Freiburg (DE); Lucinda Steward, Basel (CH); Juergen Wichmann, Steinen (DE); Thomas Woltering, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 652 days.

This patent is subject to a terminal disclaimer.

(21) Appl. No.: 11/946,947

(22) Filed: Nov. 29, 2007

(65) Prior Publication Data
US 2008/0146567 A1 Jun. 19, 2008

(30) Foreign Application Priority Data
Dec. 7, 2006 (EP) .................................. 06125604

(51) Int. Cl.
C07D 215/38 (2006.01)
(52) U.S. Cl. ........................ 546/159; 546/160
(58) Field of Classification Search ................ 546/159, 546/160
See application file for complete search history.

(56) References Cited

U.S. PATENT DOCUMENTS

| 2007/0202924 A1* | 8/2007 | Lai et al. ...................... 455/566 |
| 2007/0299074 A1 | 12/2007 | Netz et al. |
| 2008/0146567 A1* | 6/2008 | Kolczewski et al. ........ 514/235.2 |
| 2009/0227628 A1* | 9/2009 | Kolczewski et al. .......... 514/313 |

FOREIGN PATENT DOCUMENTS

| WO | WO 01/87845 A2 | 11/2001 |
| WO | 03037872 | 5/2003 |
| WO | WO 03/080579 A1 | 10/2003 |
| WO | 2004034985 | 4/2004 |
| WO | 2004080463 | 9/2004 |
| WO | WO 2004/096771 | 11/2004 |
| WO | WO 2004/106305 A1 | 12/2004 |
| WO | WO 2005/082871 | 9/2005 |
| WO | WO 2006/103511 | 10/2006 |
| WO | 2008037626 | 4/2008 |
| WO | 2008068157 | 6/2008 |

OTHER PUBLICATIONS

Giordanetto, Bioorg & Med Chem Lett, vol. 17, pp. 4232-4241, 2007.*
J.H. Burckhalter, W.H. Edgerton, J. Amer. Chem. Soc., vol. 73, pp. 4837-4839 (1951), XP002469319.
Hoyer et al., Pharmacol. Rev. vol. 46, pp. 157-204 (1994).
Thomas, D. R., Pharmacol. Ther. vol. 111(3) pp. 707-714 (2006).
Francken et al., Eur. J. Pharmacol. vol. 361(2-3) pp. 299-309 (1998).
Rees et al., FEBS Lett. vol. 355 pp. 242-246 (1994).
Doly et al., The Journal of Comparative Neurology vol. 476 pp. 316-329(2004).
Garcia-Ladona et al., 36th Annual Meeting Soc. Neurosci. (2006) Oct. 14-18th, Atlanta—Abstract 33.1.
Drescher et al., 36th Annual Meeting Soc. Neurosci. (2006) Oct. 14-18th, Atlanta—Abstract 33.2.
Noda et al., Journal of Neurochemistry vol. 84 (2003) pp. 222-232.
Dubertret et al., Journal of Psychiatric Research vol. 38 (2004) pp. 371-376.
Thomas et al., Neuropharmacology (2006) Sep.; vol. 51(3) pp. 566-577.
Barnes, Neuropharmacology pp. 1083-1152 (1999).
Birkett, NeuroReport, vol. 11 pp. 2017-2020 (2000).
Duncan, Brain Research pp. 178-185 (2000).
Iwata, Mol. Psychiatry pp. 217-219 (2001).
Pasqualetti, Mol. Brain Res. pp. 1-8 (1998).
Wang, Neurosci. Letters pp. 9-12 (2000).
Office Action issued Jul. 1, 2010 in corresponding to U.S. Appl. No. 12/394,083, filed Sep. 21, 2007.
Office Action issued Jul. 1, 2010 in corresponding U.S. Appl. No. 12/394,092, filed Feb. 27, 2009.
Office Action issued Aug. 10, 2010 in corresponding U.S. Appl. No. 12/394,083, filed Sep. 21. 2007.
Acheson, J. Chem. Soc. pp. 4440-4443 (1955).
Sprouse, Synapse pp. 111-118 (2004).

* cited by examiner

Primary Examiner — D. Margaret Seaman
(74) Attorney, Agent, or Firm — George W. Johnston; Patricia S. Rocha-Tramaloni; Kimberly J. Prior

(57) ABSTRACT

The present invention relates to 2-Aminoquinoline derivatives of general formula I

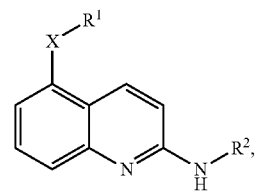

and pharmaceutically-acceptable acid-addition salts thereof, wherein $R^1$, $R^2$ and X are as defined in the specification. The compounds may be used as $5\text{-HT}_{5A}$ receptor antagonists. The present invention relates also to processes for making such a compound and a pharmaceutical composition comprising such a compound. Compounds of the present invention are useful in the prevention and/or treatment of anxiety depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders and gastrointestinal disorders.

22 Claims, No Drawings

QUINOLINES

PRIORITY TO RELATED APPLICATION(S)

This application claims the benefit of European Patent Application No. 06125604.6, filed Dec. 7, 2006, which is hereby incorporated by reference in its entirety.

FIELD OF THE INVENTION

The present invention is concerned with 2-aminoquinoline derivatives as $5\text{-HT}_{5A}$ receptor antagonists, their manufacture, and pharmaceutical compositions containing them. The active compounds of the present invention are useful in the prevention and/or treatment of, inter alia, disorders of the central nervous system, for example, anxiety depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders and gastrointestinal disorders.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., Pharmacol. Rev. 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor ($5\text{-HT}_3$) and the G-protein-coupled 7-transmembrane receptors (thirteen distinct receptors cloned to date). In addition, within the G-protein-coupled receptors, serotonin exerts its actions through an array of signal transduction mechanisms.

The $5\text{-HT}_{5A}$ receptor is one of 13 G-protein coupled 5-HT receptors and is Gi-α-coupled, inhibiting adenylate cyclase. The receptor protein DNA sequence is not closely related to that of any previously known serotonin receptor, with the best homology being 35% to the human $5\text{-HT}_{1B}$ receptor. It encodes a predicted 357 amino-acid protein, with seven putative transmembrane domains, consistent with that of a G-protein coupled receptor. The sequence is characterized by containing an intron between transmembrane domains V and VI ($5\text{-HT}_{5A}$; Barnes, N. M., & Sharp, T. (1999). A review of central 5-HT receptors and their function. Neuropharmacology 38, 1083-1152; Thomas D. R. $5\text{-HT}_{5A}$ receptors as a therapeutic target. Pharmacol Ther. (2006), 111(3):707-14; Francken B. J., Jurzak M., Vanhauwe J. F., Luyten W. H., Leysen J. E. The human 5-HT5A receptor couples to Gi/Go proteins and inhibits adenylate cyclase in HEK 293 cells. Eur. J. Pharmacol. (1998), 361(2-3):299-309. A recent review by Thomas (Pharmacology & Therapeutics, 111, 707-714; 2006) describes the potential therapeutic utility of $5\text{-HT}_{5A}$ receptor ligands for the treatment of circadian rhythm, sleep disturbances, mood disorders, schizophrenia, cognitive disorders and autism.

The human $5\text{-HT}_{5A}$ mRNA is distributed in central nervous system (CNS) areas, such as the thalamus, limbic cortex, ventrolateral amygdala, hippocampus, and hypothalamus (Pasqualetti, M., Ori, M., Nardi, I., Castagna, M., Cassano, G. B., & Marazziti, D. (1998). Distribution of the 5-HT5A serotonin receptor mRNA in the human brain. Mol Brain Res 56, 1-8). All of these central nervous system areas are implicated in either the pathology or treatment of schizophrenia and anxiety. The receptor has not been detected in peripheral organs (Rees, S., Dendaas, I., Foord, S., Goodson, S., Bull, D., Kilpatrick, G., et al. (1994). Cloning and characterization of the human $5\text{-HT}_{5A}$ serotonin receptor. FEBS Lett 355, 242-246), although it is expressed in rat superior cervical ganglia (Wang, Z. Y., Keith, I. M., Beckman, M. J., Brownfield, M. S., Vidruk, E. H. and Bisgard, G. E. (2000) 5-HT5A receptors in the carotid body chemoreception pathway of rat. Neurosci. Lett. 278, 9-12) and the spinal cord dorsal horn which may indicate the involvement of the $5\text{-HT}_{5A}$ receptor in central motor control, nociception and autonomic function such as stress induced urinary incontinence and overactive bladder (Doly, S., Fischer, J., Brisorgueil, M.-J., Verge, D. and Conrath M. 5-HT5A Receptor Localization in the Rat Spinal Cord Suggests a Role in Nociception and Control of Pelvic Floor Musculature The Journal of comparative neurology 476:316-329 (2004)). Gene association studies investigating the occurrence of several common polymorphisms within the $5\text{-HT}_{5A}$ receptor gene, such as −19G/C which shows allelic association with bipolar affective disorder, unipolar depression and schizophrenia (Birkett, J. T., Arranz, M. J., Munro, J., Osbourn, S., Kerwin, R. W., Collier, D. A., 2000. Association analysis of the 5-HT5A gene in depression, psychosis and antipsychotic response. Neuroreport 11, 2017-2020). In addition, an allelic association of the polymorphism Pro-15-Ser was found within a large proportion of Japanese schizophrenic patients (Iwata, N., Ozaki, N., Inada, T., & Goldman, D. (2001). Association of a 5-HT5A receptor polymorphism, Pro15Ser, to schizophrenia. Mol Psychiatry 6, 217-219).

Until recently, pharmacological characterization of the $5\text{-HT}_{5A}$ receptor has been limited due to lack of available selective ligands. However, in 2006 Garcia-Ladona, F. J. et al. 36th Annu. Meet. Soc. Neurosci. (2006), Oct. 14-18, Atlanta, Abstract 33.1 (see also WO 2005082871) reported preclinical evidence that certain selective $5\text{-HT}_{5A}$ receptor antagonists have an antipsychotic profile in animal models of schizophrenia by antagonizing methamphetamine and MK-801-induced hyperlocomotion, apomorphine-induced climbing and mescaline-induced scratching, while reversing disrupted social interaction (Jongen-Relo et al., 2006). Supporting evidence included, a reduction in the number of spontaneously active midbrain dopaminergic neurons observed after subchronic A-763079 treatment, suggesting potential antipsychotic-like activity. Data indicating that their $5\text{-HT}_{5A}$ receptor antagonists increase ACh levels in mPFC (Drescher, K. U. et al. 36th Annu. Meet. Soc. Neurosci. (2006), Oct. 14-18, Atlanta, Abstr. 33.2), and suggesting the potential efficacy of $5\text{-HT}_{5A}$ receptor antagonists against the cognitive deficits associated with different psychiatric disorders, in particular schizophrenia and psychosis were also presented. Thomas et al. (2006), (SB-699551-A (3-cyclopentyl-N-[2-(dimethylamino)ethyl]-N-[(40-{[(2 phenylethyl)amino]methyl}-4 biphenylyl)methyl]propanamide dihydrochloride), a novel 5-ht5A receptor-selective antagonist, enhances 5-HT neuronal function: Evidence for an autoreceptor role for the 5-ht5A receptor in guinea pig brain. Neuropharmacology. 2006 September; 51 (3):566-77) recently published microdialysis data demonstrating $5\text{-HT}_{5A}$ receptor antagonism of 5-CT-induced guinea-pig raphe neuronal firing and implying that the receptor may also act as an autoreceptor, with similar effects of those produced by anxiolytics and antidepressants. No behavioral data has been provided mainly due to species limitations. Furthermore, $5\text{-HT}_{5A}$ receptor is expressed in the hamster suprachiasmatic nucleus, a region known to be involved in circadian timing circuitry (Duncan, M. J., Jennes, L., Jefferson, J. B., Brownfield, M. S. (2000). Localization of serotonin5A receptors in discrete regions of the circadian timing system in the Syrian hamster. Brain Research 869, 178-185). Activation of both $5\text{-HT}_{5A}$ and $5\text{-HT}_7$ receptors can produce phase advances of the circadian clock in-vitro (Sprouse J, Reynolds L, Braselton J, Schmidt A. Serotonin-induced phase advances of SCN neuronal firing in vitro: a possible role for 5-HT5A receptors? Synapse 2004 November; 54(2):111-8). Furthermore, in WO 2004/096771 it is described the use of compounds, which are active on the $5\text{-HT}_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

It has been found that the compounds of formula I (described below) have a good affinity to the $5\text{-HT}_{5A}$ receptor.

The compounds are useful in the treatment or prevention of depression (which term includes bipolar depression, unipolar depression, single or recurrent major depressive episodes with or without psychotic features, catatonic features, melancholic features, atypical features or postpartum onset, seasonal affective disorders and dysthymia, and depressive disorders resulting from a general medical condition including, but not limited to, myocardial infarction, diabetes, miscarriage or abortion), anxiety disorders (which includes generalized anxiety and social anxiety disorder, panic disorders, agoraphobia, social phobia, obsessive compulsive disorders, and post-traumatic stress disorders), psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), and motor disorders (such as Parkinson's disease, dementia in Parkinson's disease, neuroleptic-induced Parkinsonism and tardive dyskinesias), as well as other psychiatric disorders and gastrointestinal disorders such as irritable bowel syndrome (WO 2004/096771).

SUMMARY OF THE INVENTION

The present invention is directed to a compound of general formula (I),

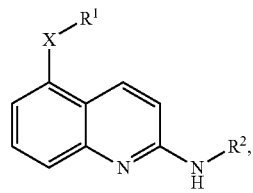

I wherein
X is selected from the group consisting of a bond, —$NR^a$—, —O—, —S—, —$SO_2$—, —$NR^b$—$S(O)_2$—, —$NR^c$—$CH_2$—, —$OCH_2$—, —$CH_2O$—, —$SCH_2$—, —$CH_2S$—, —$NR^d$—C(O)—, —$CH_2$—$NR^e$—, —$CH_2CH_2$—, —CH=CH—, —$CH_2$—S(O)$_2$—, —$OCH_2CH_2$—, —$SCH_2CH_2$—, —$NR^c CH_2 CH_2$—, —$CH_2$—$NR^d$—C(O), —$CH_2$—$NR^e$—$CH_2$—, —C($NR^k$)—, —C(O)—, —$NR^b$—$S(O)_2$—$NR^b$—, and —C(N—$OR^p$)—;
$R^1$ is mono- or bicyclic aryl, or mono- or bicyclic heteroaryl, each optionally substituted by one or more substituents independently selected from the group consisting of:
halo,
alkyl, optionally substituted by —OH or —CN,
alkoxy,
—$S(O)_2$-alkyl,
—$NR^e R^f$,
—$S(O)_2$—$NR^g R^h$,
haloalkyl,
—$CH_2$—O-alkyl,
—$(OCH_2CH_2)_m$—$OR^i$, wherein m is an integer from 1 to 3,
—$(OCH_2CH_2)_m$—$NR^q R^r$, wherein m is an integer from 1 to 3,
—$CH_2$—(N-morpholino),
—$CH_2$—$(OCH_2CH_2)_m$—$OR^j$, wherein m is an integer from 1 to 3,
hydroxy,
cyano,
nitro, and
allyl;
$R^2$ is 5- to 7-membered cycloalkyl or heterocycloalkyl, or bicyclo[2.2.1]heptyl each optionally anellated with an aromatic 5- or 6-membered carbo- or heterocycle, each ring optionally and independently substituted with one or more substituents independently selected from the group consisting of:
alkoxy,
hydroxy,
halo,
alkyl, optionally substituted by —OH or —CN,
—$S(O)_2$-alkyl,
—$NR^e R^f$,
—$S(O)_2$—$NR^g R^h$,
—$CH_2$—O-alkyl,
—$(OCH_2CH_2)_m$—$OR^i$, wherein m is an integer from 1 to 3,
—$CH_2$—$(OCH_2CH_2)_m$—$OR^j$, wherein m is an integer from 1 to 3,
cyano,
nitro, and
allyl;
$R^a$, $R^b$, $R^c$, $R^d$, $R^e$, $R^f$, $R^g$, $R^h$, $R^i$, $R^j$, $R^k$, $R^p$, $R^q$ and $R^r$ are each independently selected from the group consisting of: hydrogen, alkyl and —$(CH_2)_n$-cycloalkyl, wherein n is an integer from 0 to 3; and to a pharmaceutically-acceptable acid-addition salt thereof.

The present invention is also directed to processes for the preparation of the above compound.

The present invention is also directed to a pharmaceutical composition comprising the above compound or a pharmaceutically-acceptable acid-addition salt thereof and a pharmaceutically-acceptable excipient.

The compounds of the present invention have a good affinity to the $5\text{-HT}_{5A}$ receptor and are useful in the prevention and/or treatment of, inter alia, disorders of the central nervous system, for example, anxiety depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders and gastrointestinal disorders.

DETAILED DESCRIPTION OF THE INVENTION

The present invention is directed to a compound of general formula (I),

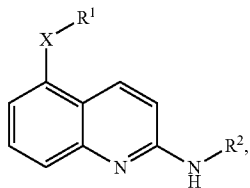

I wherein
X is selected from the group consisting of a bond, —NR$^a$—, —O—, —S—, —SO$_2$—, —NR$^b$—S(O)$_2$—, —NR$^c$—CH$_2$—, —OCH$_2$—, —CH$_2$O—, —SCH$_2$—, —CH$_2$S—, —NR$^d$—C(O)—, —CH$_2$—NR$^c$—, —CH$_2$CH$_2$—, —CH=CH—, —CH$_2$—S(O)$_2$—, —OCH$_2$CH$_2$—, —SCH$_2$CH$_2$—, —NR$^c$CH$_2$CH$_2$—, —CH$_2$—NR$^d$—C(O)—, —CH$_2$—NR$^e$—CH$_2$—, —C(NR$^k$)—, —C(O)—, —NR$^b$—S(O)$_2$—NR$^b$—, and —C(N—OR$^p$)—;

R$^1$ is mono- or bicyclic aryl, or mono- or bicyclic heteroaryl, each optionally substituted by one or more substituents independently selected from the group consisting of:
halo,
alkyl, optionally substituted by —OH or —CN,
alkoxy,
—S(O)$_2$-alkyl,
—NR$^e$R$^f$,
—S(O)$_2$—NR$^g$R$^h$,
haloalkyl,
—CH$_2$—O-alkyl,
—(OCH$_2$CH$_2$)$_m$—OR$^i$, wherein m is an integer from 1 to 3,
—(OCH$_2$CH$_2$)$_m$—NR$^q$R$^r$, wherein m is an integer from 1 to 3,
—CH$_2$—(N-morpholino),
—CH$_2$—(OCH$_2$CH$_2$)$_m$—OR$^j$, wherein m is an integer from 1 to 3,
hydroxy,
cyano,
nitro, and
allyl;

R$^2$ is 5- to 7-membered cycloalkyl or heterocycloalkyl, or bicyclo[2.2.1]heptyl each optionally anellated with an aromatic 5- or 6-membered carbo- or heterocycle, each ring optionally and independently substituted with one or more substituents independently selected from the group consisting of:
alkoxy,
hydroxy,
halo,
alkyl, optionally substituted by —OH or —CN,
—S(O)$_2$-alkyl,
—NR$^e$R$^f$,
—S(O)$_2$—NR$^g$R$^h$,
—CH$_2$—O-alkyl,
—(OCH$_2$CH$_2$)$_m$—OR$^i$, wherein m is an integer from 1 to 3,
—CH$_2$—(OCH$_2$CH$_2$)$_m$—OR$^j$, wherein m is an integer from 1 to 3,
cyano,
nitro, and
allyl;

R$^a$) R$^b$, R$^c$, R$^d$, R$^e$, R$^f$, R$^g$, R$^h$, R$^i$, R$^j$, R$^k$, R$^p$, R$^q$ and R$^r$ are each independently selected from the group consisting of: hydrogen, alkyl and —(CH$_2$)$_n$-cycloalkyl, wherein n is an integer from 0 to 3; and to a pharmaceutically-acceptable acid-addition salt thereof.

The compounds of formula I may contain some asymmetric carbon atoms. Accordingly, the present invention includes all stereoisomeric forms of the compounds of formula I, including each of the individual enantiomers and mixtures thereof, i.e. their individual optical isomers and mixtures thereof.

The compounds of the present invention have a good affinity to the 5-HT$_{5A}$ receptor and are useful in the prevention and/or treatment of, inter alia, disorders of the central nervous system, for example, anxiety depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders and gastrointestinal disorders.

In preferred embodiments, the compounds of the present invention are useful in the treatment of anxiety, depression, sleep disorders and schizophrenia.

As used herein, the term "alkyl" denotes a saturated straight- or branched-chain hydrocarbon group containing from 1 to 7 carbon atoms, for example, methyl, ethyl, propyl, isopropyl, n-butyl, iso-butyl, sec-butyl, tert-butyl and the like. Preferred alkyl groups are groups with 1-4 carbon atoms.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyls include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred haloalkyl groups are difluoro- or trifluoro-methyl or -ethyl.

The term "alkoxy" denotes a group wherein the alkyl residues are as defined above, and which is attached via an oxygen atom, i.e. a group R'—O— wherein R' is alkyl as defined above.

The terms "halo" and "halogen" each refer to chlorine, iodine, fluorine or bromine.

The term "aryl" denotes a monovalent cyclic aromatic hydrocarbon moiety consisting of a mono- or bicyclic aromatic ring, for example phenyl or naphthyl.

The term "heteroaryl" denotes an aromatic monocyclic or bicyclic ring containing one, two, three or four heteroatoms selected from nitrogen, oxygen, and sulfur as ring members, the remaining ring atoms being carbon. Preferably, the monocyclic heteroaryl ring is an aromatic 5 to 6 membered monocyclic ring containing one or two heteroatoms selected from nitrogen, oxygen, and sulfur, the remaining ring atoms being carbon. Preferably, the bicylcic heteroaryl ring is an aromatic 9 to 10 membered bicyclic ring containing one, two, three or four heteroatoms selected from nitrogen, oxygen, and sulfur, the remaining ring atoms being carbon. Examples for heteroaryl moieties include but are not limited to pyridyl, pyrazinyl, pyrimidinyl, pyridazinyl, triazinyl, thiazolyl, thienyl, furyl, pyrrolyl, imidazolyl, pyrazolyl, oxazolyl, isothiazolyl, isoxazolyl, indolyl, benzoimidazolyl, indazolyl, benzooxazolyl, 1H-pyrrolo[2,3-c]pyridinyl, benzothienyl, benzofuranyl, purinyl, quinolinyl, isoquinolinyl, quinazolinyl, quinoxalinyl, cinnolinyl, phthalazinyl, and pteridinyl. Preferred heteroaryls are imidazolyl, thienyl, pyridyl, pyrazolyl, indolyl, benzoimidazolyl, indazolyl, benzooxazolyl, and 1H-pyrrolo[2,3-c]pyridinyl.

The term "aromatic" in the above sense means the presence of an electron sextet in the ring, according to Hückel's rule.

The term "heterocycloalkyl" refers to a monovalent 5 to 7 membered saturated monocyclic ring containing one or two heteroatoms selected from nitrogen, oxygen, and sulfur as ring members, with the remaining ring atoms being carbon. Examples for heterocycloalkyl moieties are tetrahydrofuranyl, tetrahydropyranyl, pyrrolidinyl, morpholinyl, thiomorpholinyl, piperidinyl, piperidin-2-one, piperazinyl and piperazin-2-one. Preferred heterocycloalkyl moieties are tetrahydrofuranyl and tetrahydropyranyl.

The term "cycloalkyl" refers to a monovalent carbocyclic radical of 3 to 7 carbon atoms, preferably 5 to 7 carbon atoms, such as cyclopentyl, cyclohexyl or cycloheptyl.

The term "aromatic 5- or 6-membered carbo- or heterocycle" means an aromatic moiety either consisting of an aromatic hydrocarbon ring or of an aromatic ring containing one or two heteroatoms selected from nitrogen, oxygen, and sulfur as ring members, the remaining ring atoms being carbon.

The phrase "optionally anellated with an aromatic 5- or 6-membered carbo- or heterocycle" refers to an optional anellation or fusion of the above defined aromatic moiety to a 5- to 7-membered cycloalkyl or heterocycloalkyl (with the meaning as described above) or bicyclo[2.2.1]heptyl. Preferably, the anellated aromatic moiety is a 6-membered aromatic hydrocarbon ring. Each of the 5- to 7-membered cycloalkyl or heterocycloalkyl moieties or the bicyclo[2.2.1]heptyl moiety, as well as the anellated or fused aromatic 5- or 6-membered carbo- or heterocycle, may optionally and independently from each other be substituted as described herein below. Examples of a 5- to 7-membered cycloalkyl or heterocycloalkyl optionally anellated with an aromatic 5- or 6-membered carbo- or heterocycle are indanyl and 2,3-dihydrobenzofuranyl.

In the definition "$R^2$ is 5- to 7-membered cycloalkyl or heterocycloalkyl, optionally anellated with an aromatic 5- or 6-membered carbo- or heterocycle, each optionally and independently substituted with one or more . . . ", the phrase "each optionally and independently substituted with one or more . . . " means that, optionally, residues may be attached either to the 5- to 7-membered cycloalkyl or heterocycloalkyl, or to the anellated aromatic 5- or 6-membered carbo- or heterocycle, or to both. Further, the optional substituents may be independently selected from the group as given above. Moreover, "one or more" in principle means that from one to every position may be substituted with such a substituent. In case $R^2$ bears "one or more" substituents, preferably one or two substituents are attached to either the 5- to 7-membered cycloalkyl or heterocycloalkyl, or the anellated aromatic 5- or 6-membered carbo- or heterocycle, or both. Thereby, the optional substituents of $R^2$ may be selected from the group as defined above. In certain embodiments of the invention, the optional substituents of $R^2$ are selected from alkoxy, hydroxy, halo, or alkyl. Even more preferably, the optional substituents of $R^2$ are selected from alkoxy or hydroxy.

As used herein, "one or more" preferably denotes one, two or three.

The term "pharmaceutically-acceptable acid-addition salt" embraces salts of a compound of formula I with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like, the salt not being toxic and not interfering with the ability of the compound of formula I to elicit the biological or medical response of a tissue system, animal or human, that is being sought by the researcher, veterinarian, medical doctor or other clinician.

In a preferred embodiment, the compound of the present invention is a compound of formula I in which X is selected from the group consisting of a bond, —$NR^a$—, —O—, —S—, —$SO_2$—, —$NR^bS(O)_2$—, —$NR^cCH_2$—, —$OCH_2$—, —$CH_2O$—, —$SCH_2$—, —$CH_2S$—, —$NR^dC(O)$—, —$CH_2NR^c$—, —$CH_2CH_2$—, —CH=CH—, —$CH_2S(O)_2$—, —$OCH_2CH_2$—, —$SCH_2CH_2$—, and —$NR^cCH_2CH_2$—, $R^1$ is mono- or bicyclic aryl, or mono- or bicyclic heteroaryl, each optionally substituted by one or more substituents independently selected from the group consisting of
halo,
alkyl, optionally substituted by —OH or —CN,
alkoxy,
—$S(O)_2$-alkyl,
—$NR^eR^f$,
—$S(O)_2$—$NR^gR^h$,
haloalkyl,
—$CH_2$—O-alkyl,
—$(OCH_2CH_2)_m$—$OR^i$, wherein m is an integer from 1 to 3,
—$CH_2$—$(OCH_2CH_2)_m$—$OR^j$, wherein m is an integer from 1 to 3,
hydroxy,
cyano,
nitro, and allyl;

$R^2$ is 5- to 7-membered cycloalkyl or heterocycloalkyl, optionally anellated with an aromatic 5- or 6-membered carbo- or heterocycle, each ring optionally and independently substituted with one or more substituents independently selected from the group consisting of:
alkoxy,
hydroxy,
halo,
alkyl, optionally substituted by —OH or —CN,
—$S(O)_2$-alkyl,
—$NR^eR^f$,
—$S(O)_2$—$NR^gR^h$,
—$CH_2$—O-alkyl,
—$(OCH_2CH_2)_m$—$OR^i$, wherein m is an integer from 1 to 3,
—$CH_2$—$(OCH_2CH_2)_m$—$OR^j$, wherein m is an integer from 1 to 3,
cyano,
nitro, and andallyl;

$R^a$, $R^b$, $R^c$, $R^d$, $R^e$, $R^f$, $R^g$, $R^h$, $R^i$ and $R^j$ are each independently selected from the group consisting of hydrogen, alkyl or —$(CH_2)_n$-cycloalkyl, wherein n is from 0 to 3;

or a pharmaceutically-acceptable acid-addition salt thereof.

Certain embodiments of the invention relate to compounds of formula (I) wherein

X is selected from the group consisting of a bond, —$NR^a$—, —O—, —S—, —$NR^bS(O)_2$—, —$NR^cCH_2$—, —$OCH_2$—, —$CH_2O$—, —$SCH_2$—, —$NR^dC(O)$—, —CH$_2$NR$^c$—, —CH$_2$CH$_2$—, —CH=CH—, —CH$_2$S(O)$_2$—, and —OCH$_2$CH$_2$—; and R$^a$, R$^b$, R$^c$ and R$^d$ are each independently hydrogen or alkyl; or a pharmaceutically-acceptable acid-addition salt thereof.

In certain embodiments, the invention relates to compounds of formula (I) wherein X is selected from the group consisting of —NR$^a$—, —O—, —NR$^b$S(O)$_2$—, —NR$^c$CH$_2$—, —OCH$_2$—, and —NR$^d$C(O)— and R$^a$, R$^b$, R$^c$ and R$^d$ are each independently hydrogen or alkyl; or a pharmaceutically-acceptable acid-addition salt thereof. Preferably, R$^a$ is hydrogen, R$^b$ is hydrogen or methyl, R$^c$ is hydrogen and R$^d$ is hydrogen.

In certain embodiments, the "mono- or bicyclic aryl, or mono- or bicyclic heteroaryl" of R$^1$ is selected from the group consisting of phenyl, indolyl, imidazolyl, thienyl, pyridyl, and pyrazolyl, optionally substituted as described above. When aryl is phenyl, preferably phenyl is substituted in the 3, 4, and/or 5-position.

Certain embodiments of the invention relate to compounds of formula (I) wherein
R$^1$ is mono- or bicyclic aryl, or mono- or bicyclic heteroaryl, each optionally substituted by one or more substituents independently selected from the group consisting of:
halo,
alkyl, optionally substituted by —OH,
alkoxy,
—S(O)$_2$-alkyl,
—NR$^e$R$^f$,
—S(O)$_2$—NR$^g$R$^h$,
haloalkyl,
—CH$_2$—O-alkyl,
—(OCH$_2$CH$_2$)$_m$—OR$^i$, wherein m is 1, and
—(CH$_2$—O—CH$_2$CH$_2$)$_m$—OR$^j$, wherein m is 1; and
R$^e$, R$^f$, R$^g$, R$^h$, R$^i$ and R$^j$ are each independently hydrogen, alkyl or —(CH$_2$)$_n$-cycloalkyl, wherein n is from 0 to 3; or a pharmaceutically-acceptable acid-addition salt thereof.

In certain embodiments, R$^e$ and R$^f$ are each independently hydrogen, alkyl or —(CH$_2$)$_n$-cycloalkyl, wherein n is an integer from 0 to 3; and R$^g$, R$^h$, R$^i$ and R$^j$ are each independently hydrogen or alkyl. In certain embodiments, —NR$^e$R$^f$ is a cyproylmethyl-amino moiety.

In certain embodiments, the invention relates to a compound of formula (I) wherein R$^1$ is a mono- or bicyclic aryl, or mono- or bicyclic heteroaryl, each optionally substituted by one or more substituents independently selected from the group consisting of halo, alkyl, alkoxy, —S(O)$_2$-alkyl, and —NR$^e$R$^f$, wherein R$^e$ and R$^f$ are each independently hydrogen, alkyl or —(CH$_2$)$_n$-cycloalkyl, wherein n is an integer from 0 to 3; or a pharmaceutically-acceptable acid-addition salt thereof.

Certain embodiments of the invention encompass a compound of formula I in which R$^1$ is selected from the group consisting of: 4-chlorophenyl, 4-fluorophenyl, 3,5-difluorophenyl, 3,4,5-trifluorophenyl, 3-methoxyphenyl, 3-methanesulfonylphenyl, 4-cyclopropylmethyl-amino-phenyl, pyridin-3-yl, 5-fluoro-pyridin-3-yl, 5-chloro-thiophene-2-yl, 1H-imidazol-4-yl, 1H-imidazol-2-yl, 2-methyl-1H-imidazol-4-yl, 3-methyl-3H-imidazol-4-yl, 1H-pyrazol-3-yl, 1-methyl-1H-pyrazol-4-yl, or 1H-indol-4-yl; or a pharmaceutically-acceptable acid-addition salt of such a compound.

In certain embodiments, R$^1$ is optionally-substituted phenyl, indolyl, imidazolyl, thienyl, pyridyl, or pyrazolyl.

In certain embodiments, R$^2$ is a 5- to 7-membered cycloalkyl or heterocycloalkyl selected from the group consisting of cyclopentyl, cycloheptyl, cyclohexyl, tetrahydrofuran-3yl, and tetrahydropyran-4-yl.

In certain embodiments, R$^2$ is a 5- to 7-membered cycloalkyl or heterocycloalkyl, optionally anellated with an aromatic 5- or 6-membered carbo- or heterocycle. The aforementioned rings may, for example, be each optionally and independently substituted with one or more substituents selected from the group consisting of alkoxy, hydroxy, halo, or alkyl. Preferably, R$^2$, being a 5- to 7-membered cycloalkyl or heterocycloalkyl, may optionally be anellated with a 6-membered aromatic carbocycle or an aromatic 5- or 6-membered heterocycle. Certain embodiments of the invention relate to compounds with R$^2$ being selected from the group consisting of indan-1-yl, indan-2-yl, chroman-4-yl, 1,2,3,4-tetrahydro-naphthalen-1-yl, cyclopentyl, hyclohexyl and cycloheptyl, each optionally substituted by one or two alkoxy or hydroxy groups.

Preferably, R$^2$ is selected from the group consisting of indan-1-yl, 7-methoxy-indan-1-yl, 6-methoxy-indan-1-yl, 4-methoxy-indan-1-yl, 2-hydroxy-indan-1-yl, 2-(1S,2R)-hydroxy-indan-1-yl, 2-(1R,2S)-hydroxy-indan-1-yl, indan-2-yl, 2,3-dihydro-benzofuran-3-yl, 1,2,3,4-tetrahydro-naphthalene-1-yl, 5,8-dimethoxy-1,2,3,4-tetrahydro-naphthalene-1-yl, chroman-4-yl, cyclopentyl, cyclohexyl, and cycloheptyl.

In certain embodiments, R$^2$ is selected from the group consisting of: cyclopentyl, cyclohexyl, cycloheptyl, tetrahydrofuran-3-yl, and tetrahydropyran-4-yl, optionally anellated with a benzo ring, each ring optionally and independently substituted with one or more substituents independently selected from the group consisting of: alkoxy, hydroxy, halo, and alkyl.

Certain embodiments of the invention are concerned with compounds of the general formula (I)

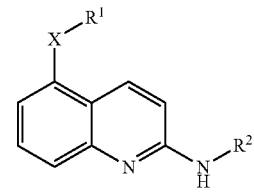

wherein
X is selected from the group consisting of a bond, —NR$^a$—, —O—, —S—, —NR$^b$S(O)$_2$—, —NR$^c$CH$_2$—, —OCH$_2$—, —CH$_2$O—, —SCH$_2$—, —NR$^d$C(O)—, —CH$_2$NR$^c$—, —CH$_2$CH$_2$—, —CH=CH—, —CH$_2$S(O)$_2$—, and —OCH$_2$CH$_2$—;
R$^1$ is mono- or bicyclic aryl, or mono- or bicyclic heteroaryl, each optionally substituted by one or more substituents independently selected from the group consisting of:
halo,
alkyl, optionally substituted by —OH,
alkoxy,
—S(O)$_2$-alkyl,
—NR$^e$R$^f$,
—S(O)$_2$—NR$^g$R$^h$,
haloalkyl,
—CH$_2$—O-alkyl,
—(OCH$_2$CH$_2$)$_m$—OR$^i$, wherein m is 1, and
—CH$_2$—(OCH$_2$CH$_2$)$_m$—OR$^j$, wherein m is 1;
R$^2$ is 5- to 7-membered cycloalkyl or heterocycloalkyl, optionally anellated with an aromatic 5- or 6-membered carbo- or heterocycle, each ring optionally and independently substituted with one or more substituents independently selected from the group consisting of:
alkoxy,
hydroxy,
halo, and
alkyl;
$R^a, R^b, R^c, R^d, R^e, R^f, R^g, R^h, R^i$ and $R^j$ are each independently selected from the group consisting of hydrogen, alkyl or —(CH$_2$)$_n$-cycloalkyl, wherein n is from 0 to 3;
or a pharmaceutically-acceptable acid-addition salt thereof.

Certain embodiments of the invention are concerned with compounds of the general formula (I)

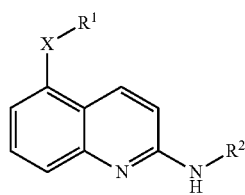

I wherein
X is selected from the group consisting of —NR$^a$—, —O—, —NR$^b$S(O)$_2$—, —NR$^c$CH$_2$—, —OCH$_2$—, and —NR$^d$C(O)—;
R$^1$ is mono- or bicyclic aryl, or mono- or bicyclic heteroaryl, each optionally substituted by one or more substituents independently selected from the group consisting of:
halo,
alkyl,
alkoxy,
—S(O)$_2$-alkyl, and
—NR$^e$R$^f$;
R$^2$ is 5- to 7-membered cycloalkyl or heterocycloalkyl, optionally anellated with an aromatic 5- or 6-membered carbo- or heterocycle, each ring optionally and independently substituted with one or more substituents independently selected from the group consisting of alkoxy, and hydroxyl;
R$^a$, R$^b$, R$^c$, R$^d$, R$^e$, and R$^f$ are each independently selected from the group consisting of hydrogen, alkyl and —(CH$_2$)$_n$-cycloalkyl, wherein n is from 0 to 3;
or a pharmaceutically acceptable acid addition salt thereof.

Preferred compounds of the present invention wherein X is —NH(SO$_2$)—, are for example the following compounds:
4-Fluoro-N-[2-((R)-indan-1-ylamino)-quinolin-5-yl]-benzenesulfonamide,
5-Chloro-thiophene-2-sulfonic acid [2-((R)-indan-1-ylamino)-quinolin-5-yl]-amide,
rac-N-[2-(Chroman-4-ylamino)-quinolin-5-yl]-3,5-difluoro-benzenesulfonamide,
3,5-Difluoro-N-[2-((R)-indan-1-ylamino)-quinolin-5-yl]-benzenesulfonamide,
rac-N-[2-(2,3-Dihydro-benzofuran-3-ylamino)-quinolin-5-yl]-3,4,5-trifluoro-benzenesulfonamide,
3,4,5-Trifluoro-N-[2-(indan-2-ylamino)-quinolin-5-yl]-benzenesulfonamide,
rac-3,4,5-Trifluoro-N-[2-(6-methoxy-indan-1-ylamino)-quinolin-5-yl]-benzenesulfonamide,
3,4,5-Trifluoro-N-[2-((R)-indan-1-ylamino)-quinolin-5-yl]-benzenesulfonamide,
rac-3,4,5-Trifluoro-N-[2-(7-methoxy-indan-1-ylamino)-quinolin-5-yl]-benzenesulfonamide,
(+)-3,4,5-Trifluoro-N-[2-(6-methoxy-indan-1-ylamino)-quinolin-5-yl]-benzenesulfonamide,
rac-4-Fluoro-N-[2-(6-methoxy-indan-1-ylamino)-quinolin-5-yl]-benzenesulfonamide,
rac-N-[2-(2,3-Dihydro-benzofuran-3-ylamino)-quinolin-5-yl]-4-fluoro-benzenesulfonamide,
N-(2-Cyclopentylamino-quinolin-5-yl)-4-fluoro-benzenesulfonamide,
rac-4-Fluoro-N-[2-(7-methoxy-indan-1-ylamino)-quinolin-5-yl]-benzenesulfonamide,
(+)-4-Fluoro-N-[2-(6-methoxy-indan-1-ylamino)-quinolin-5-yl]-benzenesulfonamide,
N-[2-(5,8-Dimethoxy-1,2,3,4-tetrahydro-naphthalen-1-ylamino)-quinolin-5-yl]-4-fluoro-benzenesulfonamide,
(+)-N-{2-[(2,3-Dihydro-benzofuran-3-yl)amino]-quinolin-5-yl}-4-fluoro-benzenesulfonamide,
N-[2-(2,3-Dihydro-benzofuran-3-ylamino)-quinolin-5-yl]-3,5-difluoro-benzenesulfonamide,
3,5-Difluoro-N-[2-(7-methoxy-indan-1-ylamino)-quinolin-5-yl]-benzenesulfonamide,
3,5-Difluoro-N-[2-(4-methoxy-indan-1-ylamino)-quinolin-5-yl]-benzenesulfonamide,
(+)-N-{2-[(2,3-Dihydro-benzofuran-3-yl)amino]-quinolin-5-yl}-3,5-difluoro-benzenesulfonamide,
3,5-Difluoro-N-[2-((1R,2S)-2-hydroxy-indan-1-ylamino)-quinolin-5-yl]-benzenesulfonamide,
4-(Cyclopropylmethyl-amino)-N-[2-((R)-indan-1-ylamino)-quinolin-5-yl]-benzenesulfonamide,
1-Methyl-1H-imidazole-4-sulfonic acid [2-((R)-indan-1-ylamino)-quinolin-5-yl]-amide,
N-(2-Cyclohexylamino-quinolin-5-yl)-4-fluoro-benzenesulfonamide,
3,5-Difluoro-N-[2-((1S,2R)-2-hydroxy-indan-1-ylamino)-quinolin-5-yl]-benzenesulfonamide,
N-(2-Cycloheptylamino-quinolin-5-yl)-4-fluoro-benzenesulfonamide,
rac 3,5-Difluoro-N-[2-(8-methoxy-1,2,3,4-tetrahydro-naphthalen-1-ylamino)-quinolin-5-yl]-benzenesulfonamide; and
pharmaceutically-acceptable acid-addition salts of the above compounds.

Preferred compounds of the present invention wherein X is —OCH$_2$— are for example the following compounds:
[5-(4-Fluoro-benzyloxy)-quinolin-2-yl]-(R)-indan-1-yl-amine,
(R)-Indan-1-yl-[5-(3-methoxy-benzyloxy)-quinolin-2-yl]-amine,
(R)-Indan-1-yl-[5-(pyridin-3-ylmethoxy)-quinolin-2-yl]-amine; and
pharmaceutically-acceptable acid-addition salts of the above compounds.

Preferred compounds of the present invention wherein X is —NHCH$_2$—, are for example the following compounds:
N5-(3,5-Difluoro-benzyl)-N2-(R)-indan-1-yl-quinoline-2,5-diamine,
N2-(R)-Indan-1-yl-N5-pyridin-3-ylmethyl-quinoline-2,5-diamine,
rac-N5-(3,5-Difluoro-benzyl)-N2-(2,3-dihydro-benzofuran-3-yl)-quinoline-2,5-diamine,
rac-N2-(2,3-Dihydro-benzofuran-3-yl)-N5-pyridin-3-ylmethyl-quinoline-2,5-diamine,
rac-N2-(6-Methoxy-indan-1-yl)-N5-pyridin-3-ylmethyl-quinoline-2,5-diamine,
rac-N5-(3-Methanesulfonyl-benzyl)-N2-(6-methoxy-indan-1-yl)-quinoline-2,5-diamine,
(+)-N2-2,3-Dihydro-benzofuran-3-yl-N5-pyridin-3-ylmethyl-quinoline-2,5-diamine, rac-N5-(3,5-Difluoro-benzyl)-N2-(6-methoxy-indan-1-yl)-quinoline-2,5-diamine,
(+)-N5-(3-Methanesulfonyl-benzyl)-N2-(6-methoxy-indan-1-yl)-quinoline-2,5-diamine,
(+)-N5-(3,5-Difluoro-benzyl)-2,3-dihydro-benzofuran-3-yl)-quinoline-2,5-diamine,
(+)-N5-(3,5-Difluoro-benzyl)-N2-(6-methoxy-indan-1-yl)-quinoline-2,5-diamine,
(+)-N2-(6-Methoxy-indan-1-yl)-N5-pyridin-3-ylmethyl-quinoline-2,5-diamine,
N5-(3H-Imidazol-4-ylmethyl)-N2-(R)-indan-1-yl-quinoline-2,5-diamine,
N2-(R)-Indan-1-yl-N5-(3-methyl-3H-imidazol-4-ylmethyl)-quinoline-2,5-diamine,
N5-(1H-Imidazol-2-ylmethyl)-N2-(R)-indan-1-yl-quinoline-2,5-diamine,
N2-(R)-Indan-1-yl-N5-(1H-pyrazol-3-ylmethyl)-quinoline-2,5-diamine,
N2-(R)-Indan-1-yl-N5-(2-methyl-1H-imidazol-4-ylmethyl)-quinoline-2,5-diamine,
N2-(R)-Indan-1-yl-N5-(1-methyl-1H-pyrazol-4-ylmethyl)-quinoline-2,5-diamine,
N2-(R)-Indan-1-yl-N5-(1H-indol-4-ylmethyl)-quinoline-2,5-diamine,
rac-N5-(1H-Indol-4-ylmethyl)-N2-(7-methoxy-indan-1-yl)-quinoline-2,5-diamine,
N5-(1H-Imidazol-4-ylmethyl)-N2-(7-methoxy-indan-1-yl)-quinoline-2,5-diamine; and
pharmaceutically-acceptable acid-addition salts of the above compounds.

Preferred compounds of the present invention wherein X is —NH—, are for example the following compounds:
N5-(4-Chloro-phenyl)-N2-(R)-indan-1-yl-quinoline-2,5-diamine,
rac-N5-(3-Methanesulfonyl-phenyl)-N2-(6-methoxy-indan-1-yl)-quinoline-2,5-diamine,
(+)-N5-(3-Methanesulfonyl-phenyl)-N2-(6-methoxy-indan-1-yl)-quinoline-2,5-diamine,
N5-(5-Fluoro-pyridin-3-yl)-N2-(R)-indan-1-yl-quinoline-2,5-diamine; and
pharmaceutically-acceptable acid-addition salts of the above compounds.

A preferred compound of the present invention wherein X is —NCH₃(SO₂)—, is for example
4-Fluoro-N-[2-((R)-indan-1-ylamino)-quinolin-5-yl]-N-methyl-benzenesulfonamide; and pharmaceutically-acceptable acid-addition salts of the above compound.

A preferred compound of the present invention wherein X is —O—, is for example
[5-(4-Fluoro-phenoxy)-quinolin-2-yl]-(R)-indan-1-yl-amine; and pharmaceutically-acceptable acid-addition salts of the above compound.

A preferred compound of the present invention wherein X is —NH(CO)—, is for example
3,5-Difluoro-N-[2-((R)-indan-1-ylamino)-quinolin-5-yl]-benzamide; and
pharmaceutically-acceptable acid-addition salts of the above compound.

Preferred compounds of the present invention wherein X is —C(N—OH)—, are for example the following compounds:
(4-Fluoro-phenyl)-[2-((R)-indan-1-ylamino)-quinolin-5-yl]-methanone oxime,
[2-((R)-Indan-1-ylamino)-quinolin-5-yl]-phenyl-methanone oxime, (4-Chloro-phenyl)-[2-((R)-indan-1-ylamino)-quinolin-5-yl]-methanone oxime,
[2-((R)-Indan-1-ylamino)-(4-methoxy-phenyl)-quinolin-5-yl]-methanone oxime,
(3-Fluoro-phenyl)-[2-((R)-indan-1-ylamino)-quinolin-5-yl]-methanone oxime,
[2-((R)-Indan-1-ylamino)-(4-methyl-phenyl)-quinolin-5-yl]-methanone oxime, (3,5-Difluoro-phenyl)-[2-((R)-indan-1-ylamino)-quinolin-5-yl]-methanone oxime,
[2-((R)-Indan-1-ylamino)-quinolin-5-yl]-thiophen-2-yl-methanone oxime,
[2-((R)-Indan-1-ylamino)-quinolin-5-yl]-(4-morpholin-4-ylmethyl-phenyl)-methanone oxime;
and pharmaceutically-acceptable acid-addition salts of the above compounds.

Preferred compounds of the present invention wherein X is —C(NH)—, are for example the following compounds:
{5-[(4-Fluoro-phenyl)-imino-methyl]-quinolin-2-yl}-(R)-indan-1-yl-amine,
[5-(Imino-phenyl-methyl)-quinolin-2-yl]-(R)-indan-1-yl-amine; and
pharmaceutically-acceptable acid-addition salts of the above compounds.

Preferred compounds of the present invention wherein X is —C(O)—, are for example the following compounds:
(4-Fluoro-phenyl)-[2-((R)-indan-1-ylamino)-quinolin-5-yl]-methanone,
[2-((R)-Indan-1-ylamino)-quinolin-5-yl]-phenyl-methanone,
(4-Chloro-phenyl)-[2-((R)-indan-1-ylamino)-quinolin-5-yl]-methanone,
[2-((R)-Indan-1-ylamino)-(4-methoxy-phenyl)-quinolin-5-yl]-methanone,
(3-Fluoro-phenyl)-[2-((R)-indan-1-ylamino)-quinolin-5-yl]-methanone,
[2-((R)-Indan-1-ylamino)-(4-methyl-phenyl)-quinolin-5-yl]-methanone,
(3,5-Difluoro-phenyl)-[2-((R)-indan-1-ylamino)-quinolin-5-yl]-methanone,
[2-((R)-Indan-1-ylamino)-quinolin-5-yl]-thiophen-2-yl-methanone,
[2-((R)-Indan-1-ylamino)-quinolin-5-yl]-(4-morpholin-4-ylmethyl-phenyl)-methanone; and
pharmaceutically-acceptable acid-addition salts of the above compounds.

Further preferred compounds of the present invention are the following compounds:
rac-exo-N-[2-(Bicyclo[2.2.1]hept-2-ylamino)-quinolin-5-yl]-4-fluoro-benzenesulfonamide,
rac-1-Methyl-1H-indole-4-sulfonic acid [2-(7-methoxy-indan-1-ylamino)-quinolin-5-yl]-amide,
rac-3,5-Difluoro-N-[2-(1,2,3,4-tetrahydro-naphthalen-1-ylamino)-quinolin-5-yl]-benzenesulfonamide,
(R)-Indan-1-yl-(5-phenyl-quinolin-2-yl)-amine,
N5-[2-(2-Dimethylamino-ethoxy)-benzyl]-N2-(R)-indan-1-yl-quinoline-2,5-diamine,
(R)-Indan-1-yl-(5-o-tolyl-quinolin-2-yl)-amine,
(R)-Indan-1-yl-(5-pyridin-3-yl-quinolin-2-yl)-amine,
rac-N5-(3H-Imidazol-4-ylmethyl)-N2-(8-methoxy-1,2,3,4-tetrahydro-naphthalen-1-yl)-quinoline-2,5-diamine,
rac-N2-(8-Methoxy-1,2,3,4-tetrahydro-naphthalen-1-yl)-N5-(1H-[1,2,3]triazol-4-ylmethyl)-quinoline-2,5-diamine,
N2-(R)-Indan-1-yl-N5-(1H-indol-7-yl)-quinoline-2,5-diamine,
Rac-N5-(1H-Indol-4-ylmethyl)-N2-(8-methoxy-1,2,3,4-tetrahydro-naphthalen-1-yl)-quinoline-2,5-diamine,
N2-(R)-Indan-1-yl-N5-(1H-indol-4-yl)-quinoline-2,5-diamine,
N2-(R)-Indan-1-yl-N5-(1H-indol-5-yl)-quinoline-2,5-diamine, N2-(R)-Indan-1-yl-N5-(1H-indol-6-yl)-quinoline-2,5-diamine, (R)-Indan-1-yl-[5-(1H-indol-4-yl)-quinolin-2-yl]-amine,

[5-(2-Chloro-phenyl)-quinolin-2-yl]-(R)-indan-1-yl-amine,

N5-(2,5-Dimethyl-2H-pyrazol-3-yl)-N2-(R)-indan-1-yl-quinoline-2,5-diamine,

N5-(4-Fluoro-phenyl)-N2-(R)-indan-1-yl-quinoline-2,5-diamine,

4-Fluoro-N-[2-((R)-indan-1-ylamino)-quinolin-5-yl]-benzamide, (R)-Indan-1-yl-[5-(5-methyl-[1,2,4]oxadiazol-3-yl)-quinolin-2-yl]-amine, 4-Fluoro-N-[2-((R)-indan-1-ylamino)-quinolin-5-ylmethyl]-benzamide, {5-[(4-Fluoro-benzylamino)-methyl]-quinolin-2-yl}-(R)-indan-1-yl-amine, N-{2-[(1R)-2,3-dihydro-1H-inden-1-ylamino]quinolin-5-yl}-N'-(4-fluorophenyl)sulfamide, N5-(3,5-Difluoro-benzyl)-N2-indan-2-yl-quinoline-2,5-diamine, N2-Indan-2-yl-N5-(1H-indol-4-ylmethyl)-quinoline-2,5-diamine,

[2-((R)-Indan-1-ylamino)-(4-methyl-phenyl)-quinolin-5-yl]-methanone O-methyl-oxime; and pharmaceutically-acceptable acid-addition salts of the above compounds.

The present compounds of formula I, their starting materials, their pharmaceutically-acceptable acid-addition salts, and their optical isomers can be prepared by methods known in the art. For example, a process may be used which comprises one of the following steps:

a) reacting a compound of formula

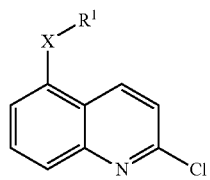

a with an amine of formula $R^2NH_2$ to give a compound of formula

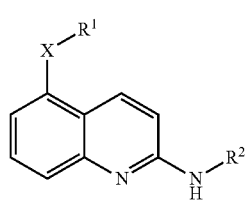

I wherein $R^1$ and $R^2$ are as defined above; or b) reacting a compound of formula

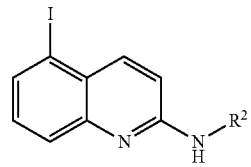

5 with an amine of formula $R^1$-$Z^1$-$NH_2$ to give a compound of formula

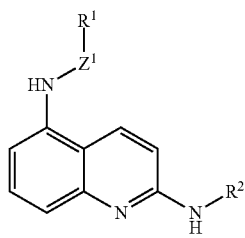

I-2 wherein $Z^1$ is —$CH_2$— or —$CH_2CH_2$— and $R^1$ and $R^2$ are as defined above; or c) reacting a compound of formula

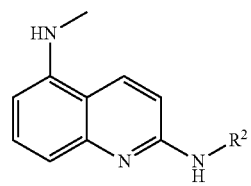

7 with a sulphonyl chloride of formula $R^1SO_2Cl$, to give a compound of formula

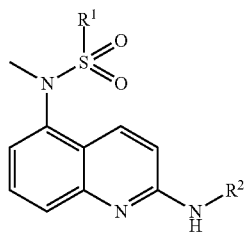

I-3 wherein $R^1$ and $R^2$ are as defined above; or d) reacting a compound of formula

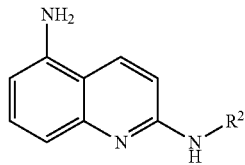

with a compound of formula R¹CHO, to give a compound of formula

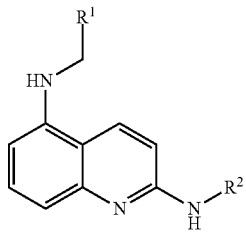

I-4 wherein R¹ and R² are as defined above; or e) reacting a compound of formula

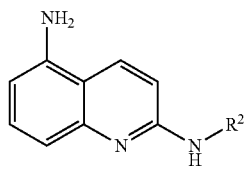

with a compound of formula R¹Z²Cl, to give a compound of formula

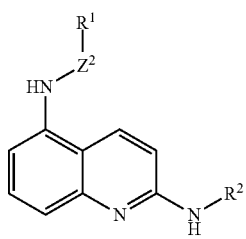

I-5 wherein Z² is —CH₂— or —CH₂CH₂— and R¹ and R² are as described above; or f) reacting a compound of formula

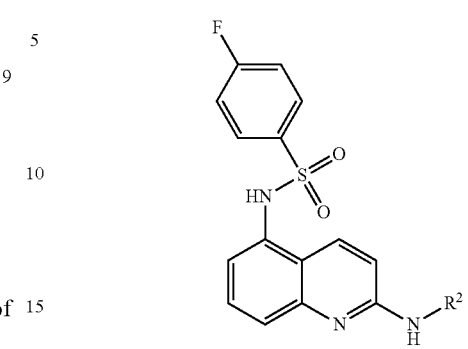

with an amine of formula R¹NH₂, to give a compound of formula

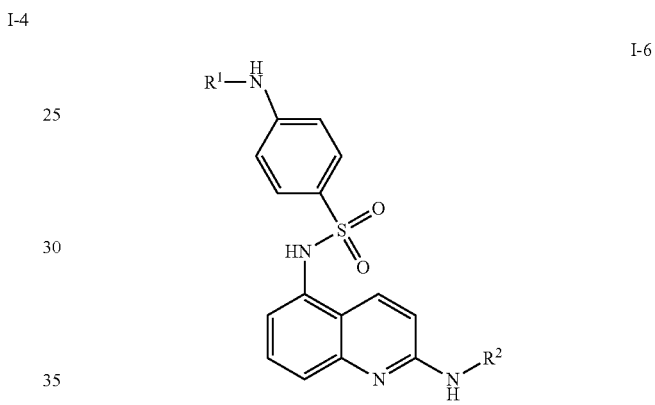

I-6 wherein R¹ is selected from alkyl or —(CH₂)ₙ-cycloalkyl, wherein n is an integer from 0 to 3 and R² is as defined above; or g) reacting a compound of formula

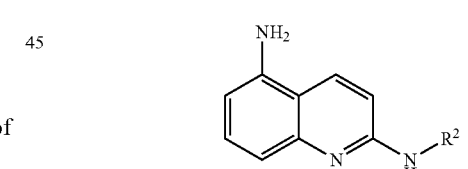

with a compound of formula R¹Br, to give a compound of formula

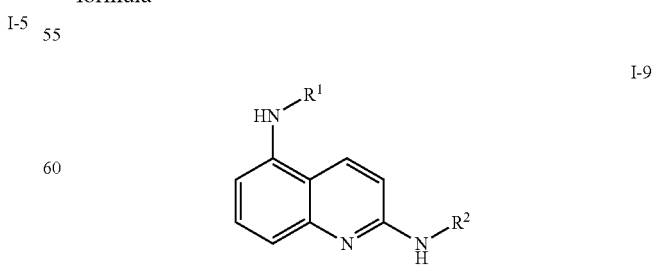

I-9 wherein R² is as defined above and R¹ is optionally substituted aryl; or h) reacting a compound of formula

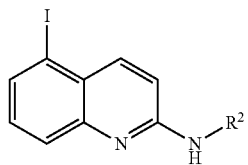

with a boronic acid of formula R¹—B(OH)₂ to give a compound of formula

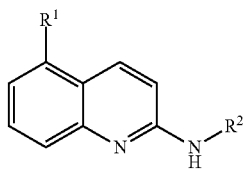
I-10 wherein R¹ and R² are as defined above; or
i) reacting a compound of formula

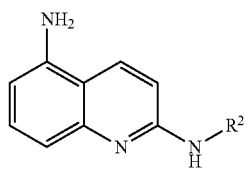
9 with a sulfamoyl chloride of formula R¹NSO₂Cl to give a compound of formula

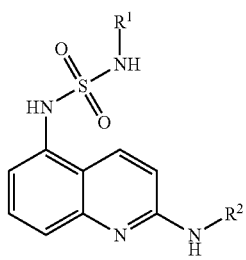
I-11 wherein R¹ and R² are as defined above; or
j) reacting a compound of formula

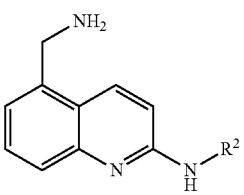
17 with a compound of formula R¹COCl to give a compound of formula

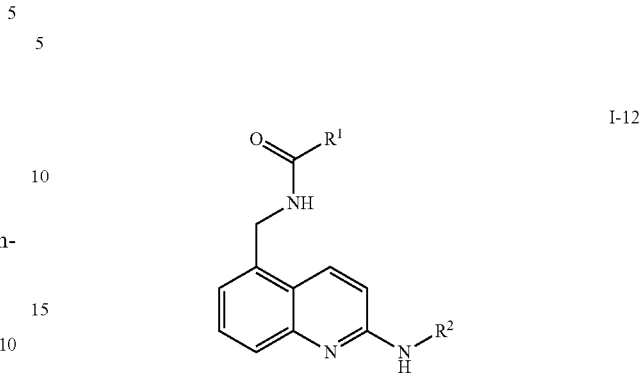
I-12 wherein R¹ and R² are as defined above; or
k) reacting a compound of formula

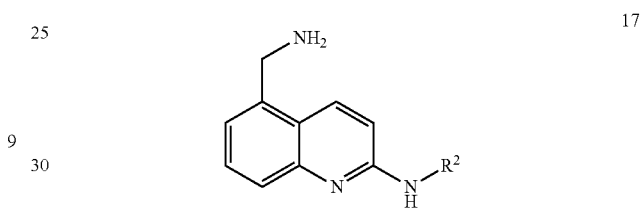
17 with a compound of formula R¹CHO to give a compound of formula

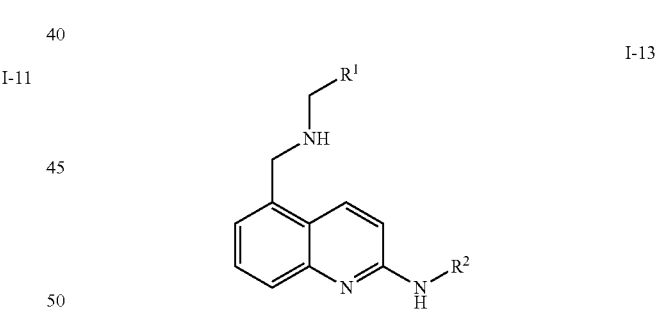
I-13 wherein R¹ and R² are as defined above; or
l) reacting a compound of formula

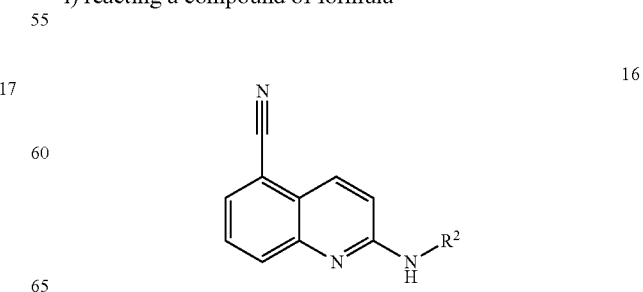
16 with a compound of formula R¹MgHal to give a compound of formula

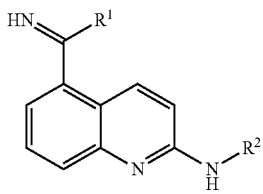

I-14 wherein R¹ and R² are defined above; or
m) reacting a compound of formula

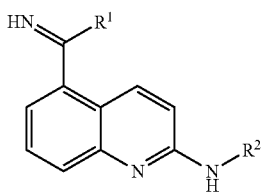

I-14 with HCl to give the corresponding ketone of formula

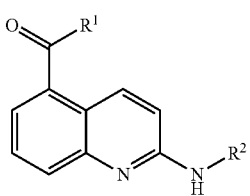

I-15 wherein R¹ and R² are as defined above; or
n) reacting a compound of formula

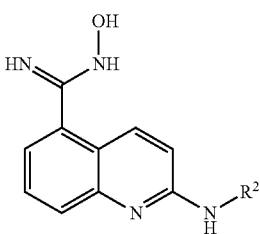

18 with acetic acid to give a compound of formula

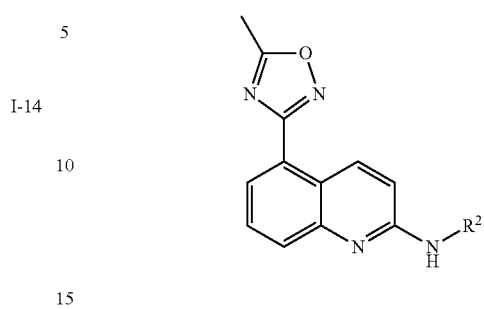

I-16 wherein R² are as defined above; or
o) reacting a compound of formula

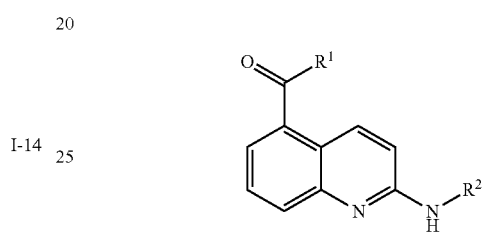

I-15 with a hydroxylamine of formula NH₂OR¹ to give the corresponding oxime of formula

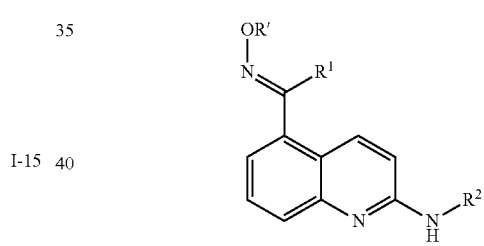

I-17 wherein R¹, R² and R¹ are as defined above;
and, if desired, converting the compound obtained into a pharmaceutically-acceptable acid-addition salt.

In examples 1-105 and in the following schemes 1 to 17, the preparation of the compounds of formula I are described in more detail. The starting materials are known compounds or may be prepared according to methods known in the art.

Compounds of formula I may be prepared in accordance with the following routes: Route 1 according to scheme 1 is described in example 1 or 13

Scheme 1

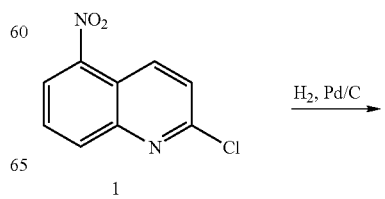

1

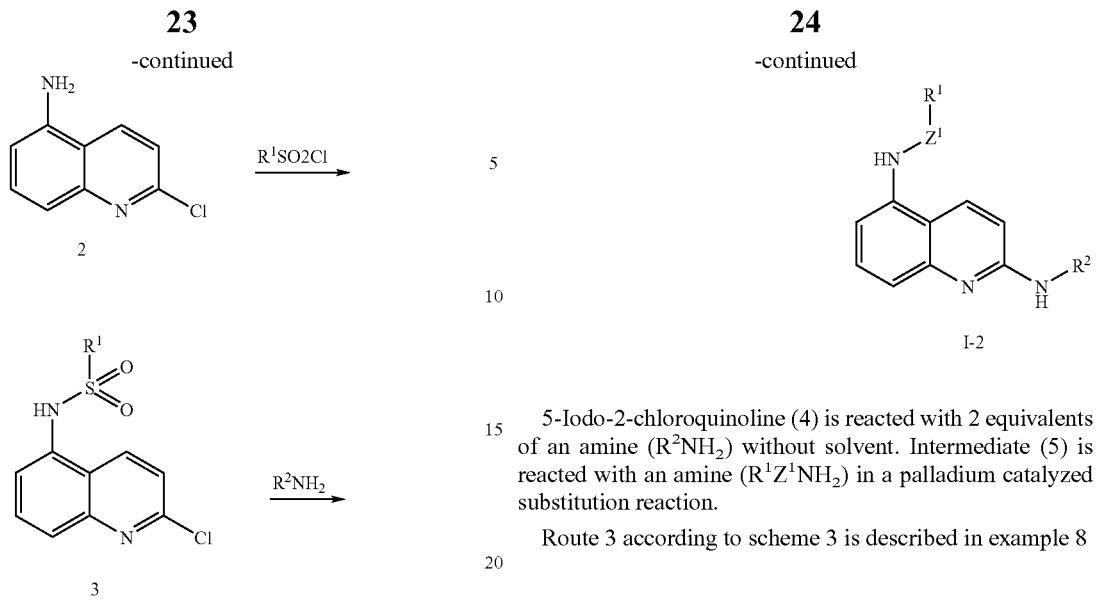

5-Nitro-2-chloroquinoline (1) is reduced with hydrogen and a palladium catalyst to the amine (2). Amine (2) is reacted with a sulfonylchloride ($R^1SO_2Cl$) in pyridine. Intermediate (3) is reacted with 2 equivalents of an amine ($R^2NH_2$) without solvent.

Route 2 according to scheme 2 is described in example 6

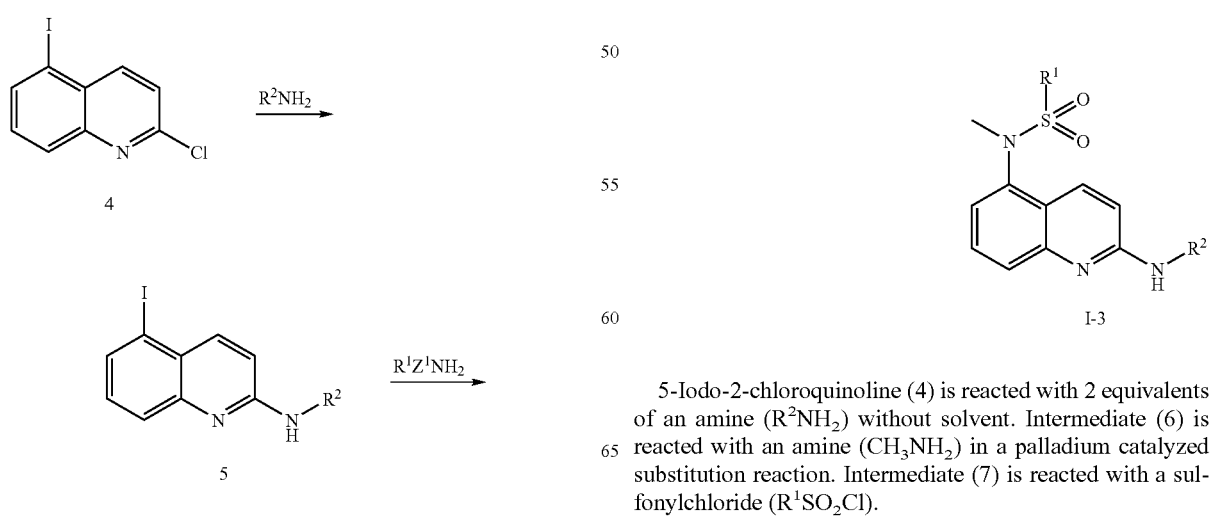

5-Iodo-2-chloroquinoline (4) is reacted with 2 equivalents of an amine ($R^2NH_2$) without solvent. Intermediate (5) is reacted with an amine ($R^1Z^1NH_2$) in a palladium catalyzed substitution reaction.

Route 3 according to scheme 3 is described in example 8

5-Iodo-2-chloroquinoline (4) is reacted with 2 equivalents of an amine ($R^2NH_2$) without solvent. Intermediate (6) is reacted with an amine ($CH_3NH_2$) in a palladium catalyzed substitution reaction. Intermediate (7) is reacted with a sulfonylchloride ($R^1SO_2Cl$).

Route 4 according to scheme 4 is described in example 43

Scheme 4

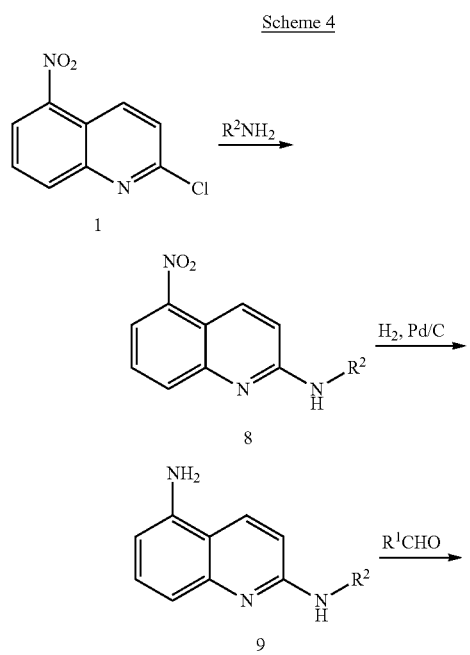

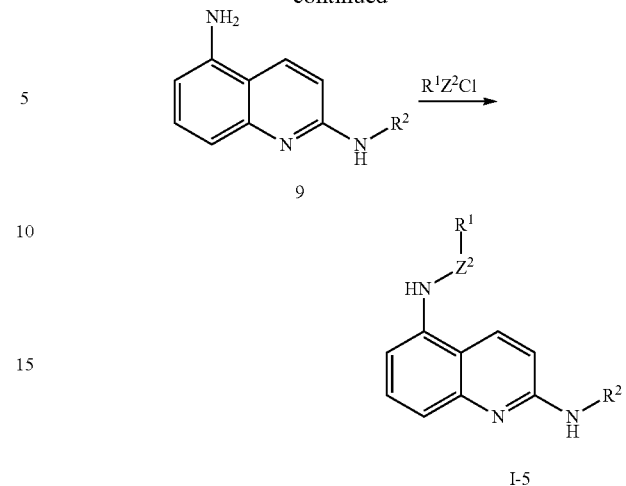

5-Nitro-2-chloroquinoline (1) reacted with 2 equivalents of an amine ($R^2NH_2$) without solvent. The nitro-compound (8) is reduced with hydrogen and a palladium catalyst to the amine (9) which is reacted with a sulfonylchloride ($R^1Z^2Cl=R^1Z'SO_2Cl$) or an acid chloride ($R^1Z^2Cl=R^1Z'COCl$) in pyridine.

Route 6 according to scheme 6 is described in example 46

Scheme 6

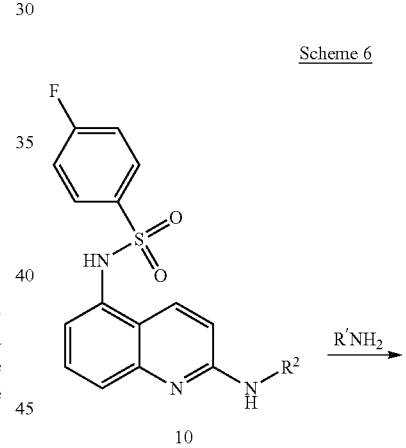

5-Nitro-2-chloroquinoline (1) reacted with 2 equivalents of an amine ($R^2NH_2$) without solvent. The nitro-compound (8) is reduced with hydrogen and a palladium catalyst to the amine (9) which is reductively aminated with an aldehyde $R^1CHO$.

Route 5 according to scheme 5 is described in example 45

Scheme 5

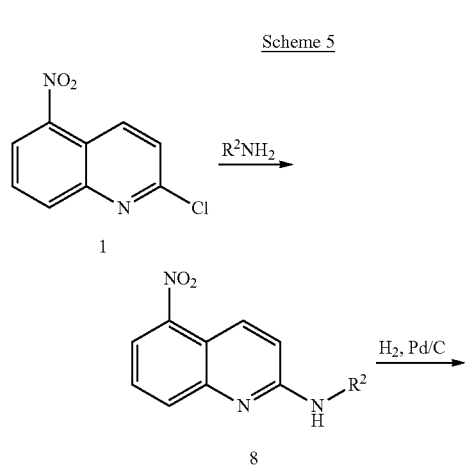

An arylfluoride compound (10) is reacted with an excess amine (R'NH2) without solvent to amine I-6.

Route 7 according to scheme 7 is described in example 2

Scheme 7

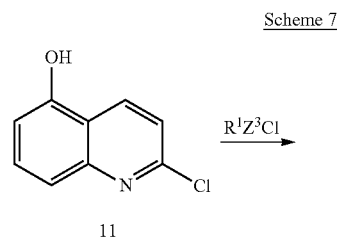

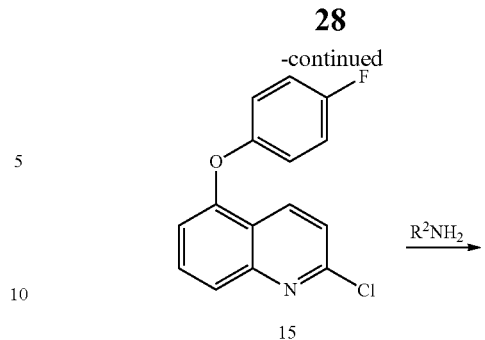

2-Chloro-5-hydroxy-quinoline (11) was alkylated in position 5 (12) and subsequently substituted in position 2 by an amine to yield compounds of generic formula I-7.

Route 8 according to scheme 8 is described in example 9:

Scheme 8

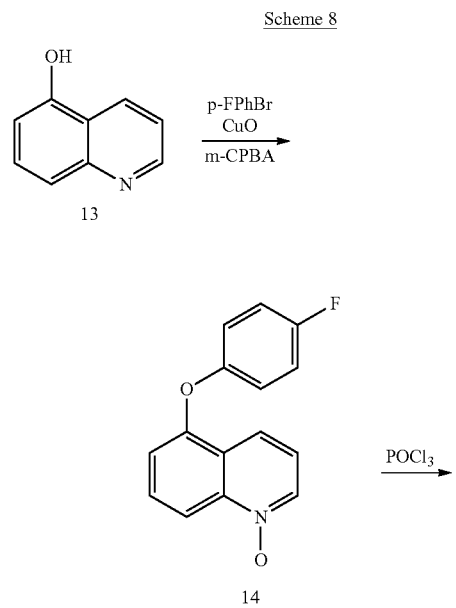

5-Hydroxy quinoline (13) was alkylated with p-bromofluorobenzene/CuO and subsequently oxidized with m-CPBA to N-oxide (14). Upon treatment with phosphorous oxychloride (neat) the 2 chloro derivative (15) was generated which was transferred to the 2-amino product (I-8).

Route 9 described according to scheme 9 in example 48

Scheme 9

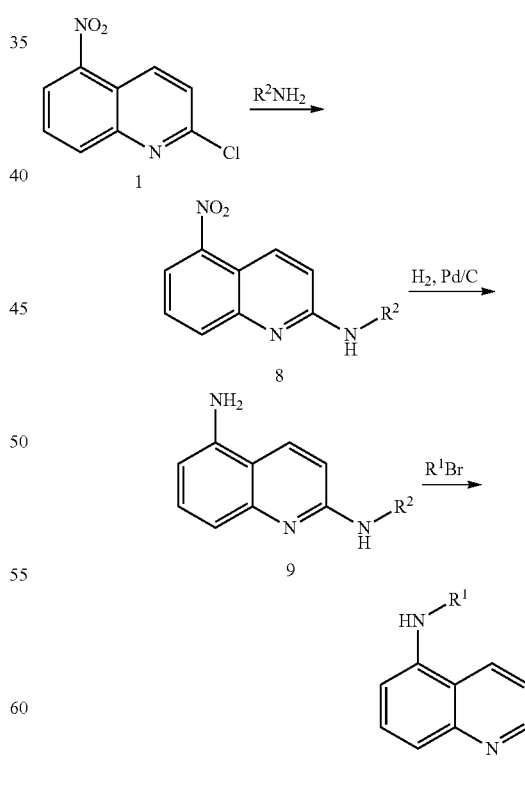

5-Nitro-2-chloroquinoline (1) reacted with 2 equivalents of an amine (R²NH₂) without solvent. The nitro-compound (8) is reduced with hydrogen and a palladium catalyst to the amine (9) which is reacted with an arylbromide in a palladium catalyzed substitution reaction.

Route 10 according to scheme 10 is described in example 63

Scheme 10

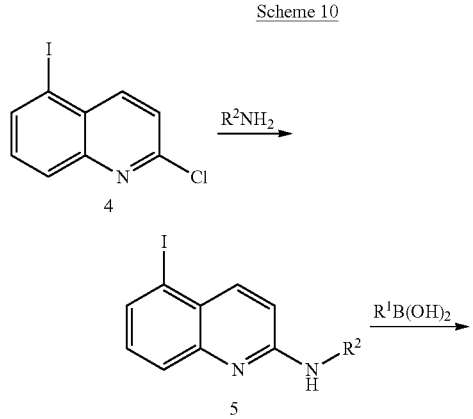

5-Iodo-2-chloroquinoline (4) is reacted with 2 equivalents of an amine ($R^2NH_2$) without solvent. Intermediate (5) is reacted with a boronic acid ($R^1B(OH)_2$) in a Suzuki reaction.

Route 11 according to scheme 11 is described in example 86

Scheme 11

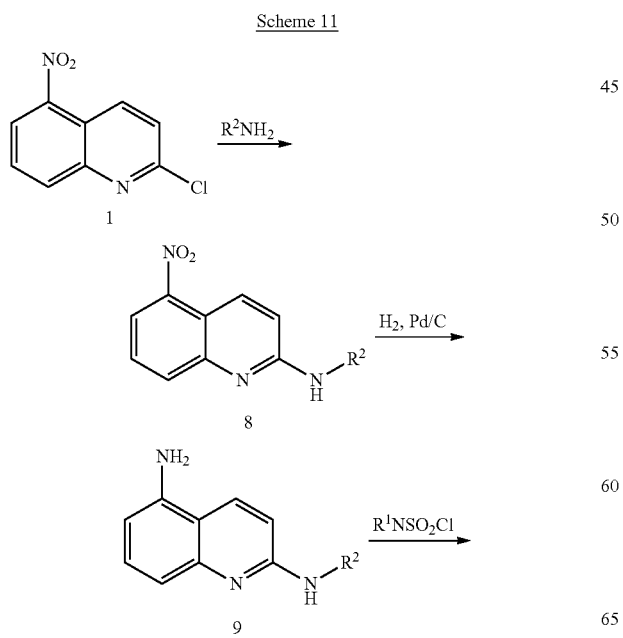

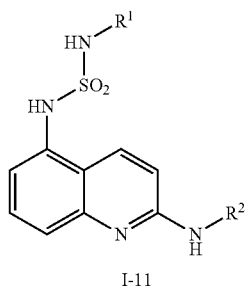

I-11

5-Nitro-2-chloroquinoline (1) reacted with 2 equivalents of an amine ($R^2NH_2$) without solvent. The nitro-compound (8) is reduced with hydrogen and a palladium catalyst to the amine (9) which is reacted with a sulfamoyl chloride ($R^1NSO_2Cl$) in pyridine.

Route 12 according to scheme 12 is described in example 80

Scheme 12

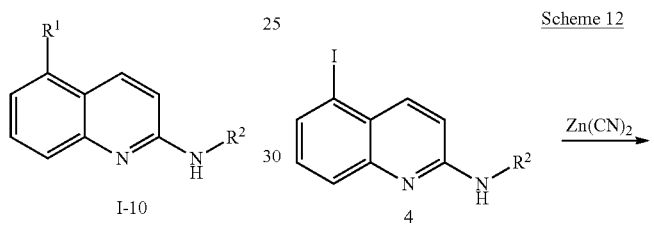

I-12

Intermediates 4 (see route 3) are reacted with zinc cyanide in a palladium catalyzed substitution reaction. The cyano group in 16 is reduced by hydrogenation to the amine (17). The amine (17) is reacted with benzoyl chloride ($Ar^1COCl$).

Route 13 according to scheme 13 is described in example 81

Scheme 13

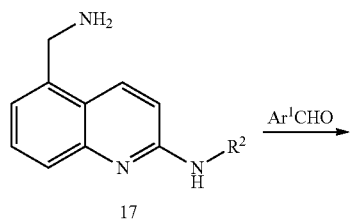

Reductive amination of benzaldehydes (Ar¹CHO) with amine (17).

Route 14 according to scheme 14 is described in example 82

Scheme 14

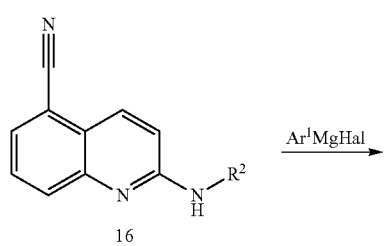

Reaction of a cyano derivative (16) with an aryl Grignard reagent (Ar¹MgHal).

Route 15 according to scheme 15 is described in example 83

Scheme 15

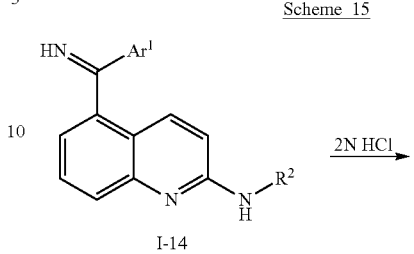

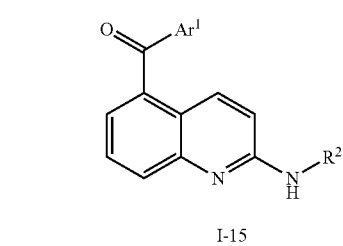

Transformation of imine (I-14) to ketone (I-15).

Route 16 according to scheme 16 is described in example 79

Scheme 16

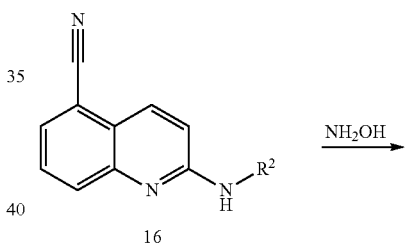

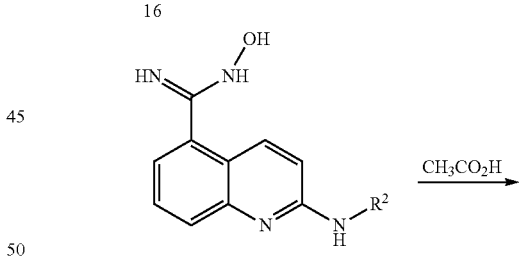

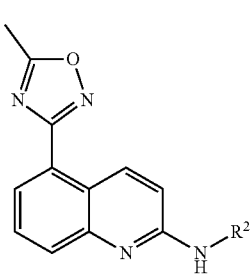

Reaction of a cyano derivatives (16) with hydroxylamine to the corresponding amidoxime (18). Formation of the methyl-oxadiazole derivative (I-16) with acetic acid.

Route 17 according to scheme 17 is described in example 89

Scheme 17

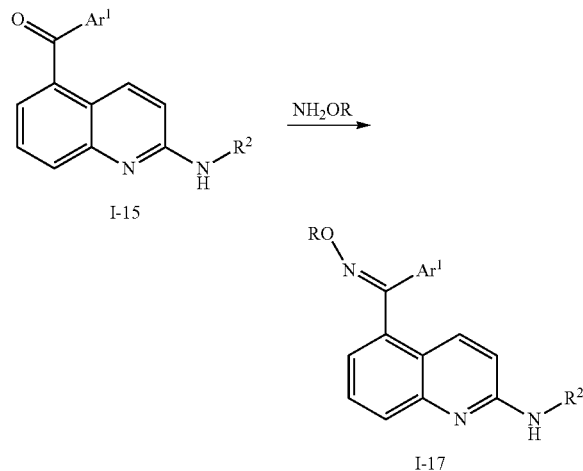

I-15

I-17

Reaction of ketone (I-15) with hydroxylamine to the corresponding oxime (I-17).

The following abbreviations have been used:
m-CPBA=meta-chloroperbenzoic acid

As mentioned earlier, the compounds of formula I and their pharmaceutically acceptable addition salts possess valuable pharmaceutical properties. It has been found that the compounds of the present invention are active on the 5-HT$_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

Another aspect of the present invention is a pharmaceutical composition comprising a compound of formula I, or a pharmaceutically-acceptable acid-addition salt thereof, and a pharmaceutically-acceptable excipient. Processes for the production of such a composition are also aspects of the present invention. Such a process comprises bringing one or more compounds of formula I and/or a pharmaceutically-acceptable salt(s) thereof and, if desired, one or more other therapeutically-valuable substances into a galenical administration form together with one or more pharmaceutically-acceptable excipients.

The term "pharmaceutically-acceptable excipient" means that the excipient is not toxic and does not interfere with the ability of the active compound(s) to elicit the biological or medical response of a tissue system, animal or human that is being sought by the researcher, veterinarian, medical doctor or other clinician. The excipient for use in the composition of the present invention may be inorganic or organic. Lactose, corn starch or derivatives thereof, talc, stearic acids or its salts and the like can be used, for example, as such excipient for tablets, coated tablets, dragées and hard gelatine capsules. Suitable excipients for soft gelatine capsules are, for example, vegetable oils, waxes, fats, semi-solid and liquid polyols and the like. Depending on the nature of the active substance, no excipients are however usually required in the case of soft gelatine capsules. Suitable excipeints for the production of solutions and syrups are, for example, water, polyols, glycerol, vegetable oil and the like. Suitable excipients for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents and antioxidants. The composition can also contain still other therapeutically valuable substances.

The pharmaceutical composition of the present invention can be administered orally, e.g. in the form of tablets, coated tablets, dragées, hard and soft gelatine capsules, solutions, emulsions or suspensions. The administration can, however, also be effected rectally, e.g. in the form of suppositories, and parenterally, e.g. in the form of injection solutions.

The present invention relates also to a method for treating or preventing a disease or disorder in a patient comprising administering a therapeutically-effective amount of a compound of the present invention to a patient. A "therapeutically-effective amount" is the amount of the subject compound that will elicit the biological or medical response of a tissue system, animal or human that is being sought by the researcher, veterinarian, medical doctor or other clinician. The above method may involve the administration of a composition which comprises a therapeutically-effective amount of the compound such as the composition described above.

The therapeutically-effective amount can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically-acceptable acid-addition salt thereof. The daily dosage may be administered as single dose or in divided doses and, in addition, the upper limit can also be exceeded when this is found to be indicated.

EXAMPLES

The following examples illustrate the invention but are not intended to limit its scope Example 1

4-Fluoro-N-[2-((R)-indan-1-ylamino)-quinolin-5-yl]-benzenesulfonamide

Step A

5-Nitro-2-chloroquinoline (CAS 13067-94-2, 5.0 g, 24 mmol) was dissolved in 500 mL ethanol and platinumoxid hydrate (176 mg, 0.718 mmol) was added. The reaction mixture was hydrogenated with a hydrogen ballon at room temperature overnight and filtered. The filtrate was evaporated off. The crude 5-amino-2-chloroquinoline (4.58 g) was used without further purification for the next step.

Step B

5-Amino-2-chloroquinoline (1.0 g, 5.6 mmol) was dissolved in 10 mL pyridine and 4-fluorobenzenesulphonylchloride (1.1 g, 5.7 mmol) was added. The reaction mixture was stirred at room temperature overnight and quenched by addition of 100 mL water and 6.8 mL acetic acid. The mixture was extracted three times with ethyl acetate (100 mL each). The organic phases ware pooled, dried with sodium sulfate, filtered and evaporated. The residue was purified by flash chromatography on silica gel (cyclohexane/ethyl acetate 100:0-

>50:50 gradient). N-(2-Chloro-quinolin-5-yl)-4-fluoro-benzenesulfonamide was obtained as a brown solid (762 mg, 40%), MS: m/e=337.1 (M+H$^+$).
Step C
N-(2-Chloro-quinolin-5-yl)-4-fluoro-benzenesulfonamide (300 mg, 0.891 mmol) and (R)-1-aminoindane (254 mg, 1.91 mmol) were stirred in a sealed tube at 120° C. overnight. The reaction mixture was purified by flash chromatography on silica gel (cyclohexane/ethyl acetate 100:0->50:50 gradient). The title compound was obtained as a yellow solid (287 mg, 74%), MS: m/e=434.1 (M+H$^+$).

Example 2

[5-(4-Fluoro-benzyloxy)-quinolin-2-yl]-(R)-indan-1-yl-amine

Step A
5-Hydroxy-2-chloroquinoline (CAS 124467-35-2, 0.6 g, 3.0 mmol) was dissolved in 15 mL acetone and potassium carbonate (555 mg, 3.0 mmol) was added. Then 4-fluorobenzylbromide (0.5 ml, 4.0 mmol) was added and the reaction mixture stirred for 18 hours at ambient temperature. The mixture was evaporated and the residue taken up in water and extracted (3×) with ethyl acetate. The combined organic phases were dried over sodium sulfate and evaporated. The residue was subjected to flash column chromatography on silica gel (heptane/ethyl acetate 90:10->80:20 gradient) to yield 2-chloro-5-(4-fluoro-benzyloxy)-quinoline as a white solid (420 mg, 44%), MS: m/e=289 (M+H$^+$).
Step B
2-Chloro-5-(4-fluoro-benzyloxy)-quinoline (100 mg, 0.347 mmol) and (R)-1-aminoindane (138 mg, 1.04 mmol) were stirred in a sealed tube at 150° C. overnight. The reaction mixture was purified by flash chromatography on silica gel (heptane/ethyl acetate 75:25). The title compound was obtained as a light brown oil (68 mg, 51%), MS: m/e=385 (M+H$^+$).

Example 3

(R)-Indan-1-yl-[5-(3-methoxy-benzyloxy)-quinolin-2-yl]-amine

The title compound, MS: m/e=397.5 (M+H$^+$), was prepared in accordance with the general method of example 2 from 5-hydroxy-2-chloroquinoline, 3-methoxy-benzylbromide and (R)-1-aminoindane.

Example 4

(R)-Indan-1-yl-[5-(pyridin-3-ylmethoxy)-quinolin-2-yl]-amine

The title compound, MS: m/e=367.5 (M+H$^+$), was prepared in accordance with the general method of example 2 from 5-hydroxy-2-chloroquinoline, 3-bromomethyl-pyridine and (R)-1-aminoindane.

Example 5

5-Chloro-thiophene-2-sulfonic acid [2-((R)-indan-1-ylamino)-quinolin-5-yl]-amide The title compound, MS: m/e=456.3 (M+H$^+$), was prepared in accordance with the general method of example 1 from 5-nitro-2-chloroquinoline, 5-chlorothiophene-2-sulfonylchloride and (R)-1-aminoindane.

Example 6

N5-(3,5-Difluoro-benzyl)-N2-(R)-indan-1-yl-quinoline-2,5-diamine

Step A
5-Iodo-2-chloroquinoline (CAS 455955-26-7, 5.0 g, 17 mmol) and (R)-1-aminoindane (4.75 g, 35 mmol) were stirred in a sealed tube at 120° C. for 2 days. The reaction mixture was purified by flash chromatography on silica gel (cyclohexane/ethyl acetate 100:0->80:20 gradient). (R)-Indan-1-yl-(5-iodo-quinolin-2-yl)-amine was obtained as a brown solid (4.30 g, 64%), MS: m/e=387.3 (M+H$^+$).
Step B
(R)-Indan-1-yl-(5-iodo-quinolin-2-yl)-amine (200 mg, 0.518 mmol) was dissolved in 2 mL dioxane. Argon was bubbled through the solution for 2 minutes to remove oxygen. 3,5-Difluorobenzylamine (153 mg, 1.07 mmol), sodium tert.-butylate (128 mg, 1.33 mmol), 1,1'-bis(diphenylphosphin)ferrocen (44 mg, 0.08 mmol) and 1,1'-bis(diphenylphosphin)ferrocen-palladium(II) chloride (21 mg, 0.03 mmol) were added. The reaction mixture was stirred in a sealed tube at 100° C. overnight. The solvent was evaporated and the residue purified by flash chromatography on silica gel (cyclohexane/ethyl acetate 100:0->50:50 gradient). The title compound was obtained as a light brown foam (153 mg, 74%), MS: m/e=402.4 (M+H$^+$).

Example 7

N5-(4-Chloro-phenyl)-N2-(R)-indan-1-yl-quinoline-2,5-diamine

The title compound, MS: m/e=386.3 (M+H$^+$), was prepared in accordance with the general method of example 6 from 5-iodo-2-chloroquinoline, (R)-1-aminoindane and 4-chloroaniline.

Example 8

4-Fluoro-N-[2-((R)-indan-1-ylamino)-quinolin-5-yl]-N-methyl-benzenesulfonamide

Step A
(R)-Indan-1-yl-(5-iodo-quinolin-2-yl)-amine was prepared from 5-iodo-2-chloroquinoline and (R)-1-aminoindane as described in example 6 step A.
Step B
$N^2$—(R)-Indan-1-yl-$N^5$-methyl-quinoline-2,5-diamine, MS: m/e=290.1 (M+H$^+$), was prepared from (R)-indan-1-yl-(5-iodo-quinolin-2-yl)-amine and methylamine (solution in methanol) in accordance with the method described in example 6 step B.
Step C
The title compound, MS: m/e=448.3 (M+H$^+$), was prepared from $N^2$—(R)-indan-1-yl-$N^5$-methyl-quinoline-2,5-diamine and 4-fluorobenzene sulfonylchloride in accordance with the method described in example 1 step B.

Example 9

[5-(4-Fluoro-phenoxy)-quinolin-2-yl]-(R)-indan-1-yl-amine

Step A

Quinolin-5-ol (CAS 124467-35-2) (1.0 g, 6.9 mmol) was dissolved in pyridine (15 mL) and potassium carbonate (0.55 g, 4 mmol), CuO (0.22 mg, 2.8 mmol) and 1-bromo-4-fluorobenzene (1.5 mL, 13.8 mmol) were added. The reaction mixture was stirred for 18 hours at 130° C. and then evaporated. The residue was dissolved in dichloro methane, filtered and concentrated. The residue was subjected to column chromatography (silica gel, heptane/ethyl acetate 9:1/4:1/1:1) to yield a yellow oil (0.66 g, 40%).
MS: m/e=240.3 (M+H$^+$)

Step B 5-(4-Fluoro-phenoxy)-quinoline (0.6 g, 2.5 mmol) were dissolved in dichloro methane (15 mL) under nitrogene and treated with m-CPBA (70%; 0.7 g, 2.8 mmol) at ambient temperature for 18 h (MS-monitoring). Then water (100 mL) was added and the aqueous phase was adjusted to pH 9 upon addition of sodium carbonate. The aqueous phase was extracted with dichloro methane (3×), the combined organic phases were dried (sodium sulfate addition), filtered and concentrated.
0.75 g (117%) N-oxide was obtained as yellow crystals.
MS: m/e=256.4 (M+H$^+$)

Step C

Phosphorous oxychloride (0.75 mL) was heated to 50° C. and 5-(4-fluoro-phenoxy) quinoline-1-oxide (0.7 g, 2.7 mmol) were added portion wise. The reaction mixture was stirred for another 60 minutes at 50° C. and after cooling to ambient temperature poured into a stirred mixture of ice in water. The aqueous phase was extracted with ethyl acetate (3×). The combined organic phases were dried on sodium sulfate, filtered and concentrated. The residue was subjected to column chromatography (silica gel, heptane/ethyl acetate 9:1/4:1/1:1) to yield white crystals (0.18 g, 24%).
MS: m/e=274.0 (M+H$^+$)

Step D

2-Chloro-5-(4-fluoro-phenoxy)-quinoline (60 mg, 0.22 mmol) and R-(−)-1-aminoindane (88 mg, 0.66 mmol) were stirred in a sealed tube at 150° C. for 16 hours. The reaction mixture was purified twice by flash chromatography on silica gel (heptane/ethyl acetate 100:0->75:25 gradient and then heptane/ethyl acetate 80:20->60:40 gradient). [5-(4-Fluoro-phenoxy)-quinolin-2-yl]-(R)-indan-1-yl-amine was obtained as a yellow oil (24 mg, 30%), MS: m/e=371 (M+H$^+$).

Example 10

N-[2-(Chroman-4-ylamino)-quinolin-5-yl]-3,5-difluoro-benzenesulfonamide

The title compound, MS: m/e=468.1 (M+H$^+$), was prepared in accordance with the general method of example 1 from 5-nitro-2-chloroquinoline, 3,5-difluorophenyl sulfonylchloride and 3,4-dihydro-2H-chromen-4-ylamine.

Example 11

3,5-Difluoro-N-[2-((R)-indan-1-ylamino)-quinolin-5-yl]-benzenesulfonamide

The title compound, MS: m/e=452.0 (M+H$^+$), was prepared in accordance with the general method of example 1 from 5-nitro-2-chloroquinoline, 3,5-difluorophenyl sulfonylchloride and (R)-1-aminoindane.

Example 12

N2-(R)-Indan-1-yl-N5-pyridin-3-ylmethyl-quinoline-2,5-diamine

The title compound, MS: m/e=367.1 (M+H$^+$), was prepared in accordance with the general method of example 6 from 5-iodo-2-chloroquinoline, (R)-1-aminoindane and 3-(aminomethyl)pyridine.

Example 13 rac-N-[2-(2,3-Dihydro-benzofuran-3-ylamino)-quinolin-5-yl]-3,4,5-trifluoro-benzenesulfonamide Step A 5-Amino-2-chloroquinoline was prepared from 5-nitro-2-chloroquinoline (CAS 13067-94-2) as described in example 1 step A.

Step B

N-(2-Chloro-quinolin-5-yl)-3,4,5-trifluoro-benzenesulfonamide (MS: m/e=371.0 (M−H$^+$), was prepared from 5-amino-2-chloroquinoline and 3,4,5-trifluorobenzenesulfonyl chloride as described in example 1 step B.

Step C

N-(2-Chloro-quinolin-5-yl)-3,4,5-trifluoro-benzenesulfonamide (150 mg, 0.402 mmol) was dissolved in 5 mL dioxane. Argon was bubbled through the solution for 2 minutes to remove oxygen. rac-2,3-Dihydro-benzofuran-3-ylamine (CAS 109926-35-4, 82 mg, 0.607 mmol), sodium tert.-butylate (97 mg, 1.01 mmol), 1,1'-bis(diphenylphosphin)ferrocen (33 mg, 0.06 mmol) and 1,1'-bis(diphenylphosphin)ferrocen-palladium(II) chloride (16 mg, 0.02 mmol) were added. The reaction mixture was stirred in a sealed tube at 120° C. for 6 hours. The solvent was evaporated and the residue purified by flash chromatography on silica gel (heptane/ethyl acetate 100:0->70:30 gradient). The title compound was obtained as a yellow foam (100 mg, 53%), MS: m/e 472.4 (M+H$^+$).

Example 14

3,4,5-Trifluoro-N-[2-(indan-2-ylamino)-quinolin-5-yl]-benzenesulfonamide

The title compound, MS: m/e=470.5 (M+H$^+$), was prepared in accordance with the general method of example 13 from 5-nitro-2-chloroquinoline, 3,4,5-trifluorobenzenesulfonyl chloride and 2-aminoindane.

Example 15 rac-3,4,5-Trifluoro-N-[2-(6-methoxy-indan-1-ylamino)-quinolin-5-yl]-benzenesulfonamide The title compound, MS: m/e=500.4 (M+H$^+$), was prepared in accordance with the general method of example 13 from 5-nitro-2-chloroquinoline, 3,4,5-trifluorobenzenesulfonyl chloride and 6-methoxyindan-1-ylamine (CAS 103028-81-5).

Example 16

3,4,5-Trifluoro-N-[2-((R)-indan-1-ylamino)-quinolin-5-yl]-benzenesulfonamide

The title compound, MS: m/e=470.5 (M+H$^+$), was prepared in accordance with the general method of example 13 from 5-nitro-2-chloroquinoline, 3,4,5-trifluorobenzenesulfonyl chloride and R-(−)-aminoindane.

Example 17 rac-N5-(3,5-Difluoro-benzyl)-N2-(2,3-dihydro-benzofuran-3-yl)-quinoline-2,5-diamine The title compound, MS: m/e=404.4 (M+H$^+$), was prepared in accordance with the general method of example 6 from 5-iodo-2-chloroquinoline, rac-2,3-dihydro-benzofuran-3-ylamine (CAS 109926-35-4) and 3,5-difluoronemzylamine.

Example 18 rac-N2-(2,3-Dihydro-benzofuran-3-yl)-N5-pyridin-3-ylmethyl-quinoline-2,5-diamine The title compound, MS: m/e=369.0 (M+H$^+$), was prepared in accordance with the general method of example 6 from 5-iodo-2-chloroquinoline, rac-2,3-dihydro-benzofuran-3-ylamine (CAS 109926-35-4) and 3-(aminomethyl)pyridine.

Example 19 rac-3,4,5-Trifluoro-N-[2-(7-methoxy-indan-1-ylamino)-quinolin-5-yl]-benzenesulfonamide The title compound, MS: m/e=500.0 (M+H$^+$), was prepared in accordance with the general method of example 13 from 5-nitro-2-chloroquinoline, 3,4,5-trifluorobenzenesulfonyl chloride and rac-7-methoxy-indane-1-ylamine.

Example 20

(+)-3,4,5-Trifluoro-N-[2-(6-methoxy-indan-1-ylamino)-quinolin-5-yl]-benzenesulfonamide Rac-3,4,5-Trifluoro-N-[2-(6-methoxy-indan-1-ylamino)-quinolin-5-yl]-benzenesulfonamide (example 15) was separated on Chiralpak AD with 15% ethanol in heptane. The title compound was eluted as the second enantiomer.

Example 21 rac-4-Fluoro-N-[2-(6-methoxy-indan-1-ylamino)-quinolin-5-yl]-benzenesulfonamide

The title compound, MS: m/e=464.1 (M+H$^+$), was prepared in accordance with the general method of example 13 from 5-nitro-2-chloroquinoline, 4-fluorobenzenesulfonyl chloride and 6-methoxyindan-1-ylamine (CAS 103028-81-5).

Example 22 rac-N-[2-(2,3-Dihydro-benzofuran-3-ylamino)-quinolin-5-yl]-4-fluoro-benzenesulfonamide The title compound, MS: m/e=436.1 (M+H$^+$), was prepared in accordance with the general method of example 13 from 5-nitro-2-chloroquinoline, 4-fluorobenzenesulfonyl chloride and rac-2,3-dihydro-benzofuran-3-ylamine (CAS 109926-35-4).

Example 23 rac-N2-(6-Methoxy-indan-1-yl)-N5-pyridin-3-ylmethyl-quinoline-2,5-diamine

The title compound, MS: m/e=397.1 (M+H$^+$), was prepared in accordance with the general method of example 6 from 5-iodo-2-chloroquinoline, 6-methoxyindan-1-ylamine (CAS 103028-81-5) and 3-(aminomethyl)-pyridine.

Example 24 rac-N5-(3-Methanesulfonyl-benzyl)-N2-(6-methoxy-indan-1-yl)-quinoline-2,5-diamine The title compound, MS: m/e=474.1 (M+H$^+$), was prepared in accordance with the general method of example 6 from 5-iodo-2-chloroquinoline, 6-methoxyindan-1-ylamine (CAS 103028-81-5) and 3-(methylsulfonyl)benzylamine.

Example 25 rac-N5-(3-Methanesulfonyl-phenyl)-N2-(6-methoxy-indan-1-yl)-quinoline-2,5-diamine The title compound, MS: m/e=460.4 (M+H$^+$), was prepared in accordance with the general method of example 6 from 5-iodo-2-chloroquinoline, 6-methoxyindan-1-ylamine (CAS 103028-81-5) and 3-methylsulfonylaniline.

Example 26

N-(2-Cyclopentylamino-quinolin-5-yl)-4-fluoro-benzenesulfonamide

The title compound, MS: m/e=385.4 (M+H$^+$), was prepared in accordance with the general method of example 13 from 5-nitro-2-chloroquinoline, 4-fluorobenzenesulfonyl chloride and cyclopentylamine.

Example 27

(+)-N2-2,3-Dihydro-benzofuran-3-yl-N5-pyridin-3-ylmethyl-quinoline-2,5-diamine

Rac-N2-(2,3-Dihydro-benzofuran-3-yl)-N5-pyridin-3-ylmethyl-quinoline-2,5-diamine (example 18) was separated on Chiralpak AD with 25% isopropanol in heptane. The title compound was eluted as the second enantiomer.

Example 28 rac-4-Fluoro-N-[2-(7-methoxy-indan-1-ylamino)-quinolin-5-yl]-benzenesulfonamide

The title compound, MS: m/e=464.1 (M+H$^+$), was prepared in accordance with the general method of example 13

Example 29 rac-N5-(3,5-Difluoro-benzyl)-N2-(6-methoxy-indan-1-yl)-quinoline-2,5-diamine

The title compound, MS: m/e=432.4 (M+H$^+$), was prepared in accordance with the general method of example 6 from 5-iodo-2-chloroquinoline, 6-methoxyindan-1-ylamine (CAS 103028-81-5) and 3-methylsulfonylaniline.

Example 30

(+)-N5-(3-Methanesulfonyl-benzyl)-N2-(6-methoxy-indan-1-yl)-quinoline-2,5-diamine Rac-N5-(3-Methanesulfonyl-benzyl)-N2-(6-methoxy-indan-1-yl)-quinoline-2,5-diamine (example 24) was separated on Chiralcel OD with 30% isopropanol in heptane. The title compound was eluted as the first enantiomer.

Example 31

(+)-N5-(3-Methanesulfonyl-phenyl)-N2-(6-methoxy-indan-1-yl)-quinoline-2,5-diamine Rac-N5-(3-Methanesulfonyl-phenyl)-N2-(6-methoxy-indan-1-yl)-quinoline-2,5-diamine (example 25) was separated on Chiralcel OD with 30% isopropanol in heptane. The title compound was eluted as the first enantiomer.

Example 32

(+)-N5-(3,5-Difluoro-benzyl)-2,3-dihydro-benzofuran-3-yl-quinoline-2,5-diamine

Rac-N5-(3,5-Difluoro-benzyl)-2,3-dihydro-benzofuran-3-yl-quinoline-2,5-diamine (example 17) was separated on Chiralcel OD with 30% isopropanol in heptane. The title compound was eluted as the first enantiomer.

Example 33

(+)-4-Fluoro-N-[2-(6-methoxy-indan-1-ylamino)-quinolin-5-yl]-benzenesulfonamide

Rac-4-Fluoro-N-[2-(6-methoxy-indan-1-ylamino)-quinolin-5-yl]-benzenesulfonamide (example 25) was separated on Chiralpak AD with 25% isopropanol in heptane. The title compound was eluted as the second enantiomer.

Example 34

N-[2-(5,8-Dimethoxy-1,2,3,4-tetrahydro-naphthalen-1-ylamino)-quinolin-5-yl]-4-fluoro-benzenesulfonamide The title compound, MS: m/e=508.4 (M+H$^+$), was prepared in accordance with the general method of example 13 from 5-nitro-2-chloroquinoline, 4-fluorobenzenesulfonyl chloride and rac-1-amino-5,8-dimethoxy-1,2,3,4-tetrahydro-naphthalene (CAS 784988-69-8).

Example 35

(+)-N5-(3,5-Difluoro-benzyl)-N2-(6-methoxy-indan-1-yl)-quinoline-2,5-diamine

Rac-N5-(3,5-Difluoro-benzyl)-N2-(6-methoxy-indan-1-yl)-quinoline-2,5-diamine (example 29) was separated on Chiralcel OD with 25% isopropanol in heptane. The title compound was eluted as the first enantiomer.

Example 36

(+)-N-{2-[(2,3-Dihydro-benzofuran-3-yl)amino]-quinolin-5-yl}-4-fluoro-benzenesulfonamide Rac-N-{2-[(2,3-Dihydro-benzofuran-3-yl)amino]-quinolin-5-yl}-4-fluoro-benzenesulfonamide (example 22) was separated on Chiralpak AD with 25% isopropanol in heptane. The title compound was eluted as the second enantiomer.

Example 37

(+)-N2-(6-Methoxy-indan-1-yl)-N5-pyridin-3-ylmethyl-quinoline-2,5-diamine

Rac-N2-(6-Methoxy-indan-1-yl)-N5-pyridin-3-ylmethyl-quinoline-2,5-diamine (example 23) was separated on Chiralpak AD with 30% isopropanol in heptane. The title compound was eluted as the first enantiomer.

Example 38

N-[2-(2,3-Dihydro-benzofuran-3-ylamino)-quinolin-5-yl]-3,5-difluoro-benzenesulfonamide The title compound, MS: m/e=454.3 (M+H$^+$), was prepared in accordance with the general method of example 13 from 5-nitro-2-chloroquinoline, 3,5-difluorobenzenesulfonyl chloride and rac-2,3-dihydro-benzofuran-3-ylamine (CAS 109926-35-4).

Example 39

3,5-Difluoro-N-[2-(7-methoxy-indan-1-ylamino)-quinolin-5-yl]-benzenesulfonamide

The title compound, MS: m/e=482.5 (M+H$^+$), was prepared in accordance with the general method of example 13 from 5-nitro-2-chloroquinoline, 3,5-difluorobenzenesulfonyl chloride and rac-7-methoxy-indane-1-ylamine.

Example 40

3,5-Difluoro-N-[2-(4-methoxy-indan-1-ylamino)-quinolin-5-yl]-benzenesulfonamide

The title compound, MS: m/e=482.5 (M+H$^+$), was prepared in accordance with the general method of example 13 from 5-nitro-2-chloroquinoline, 3,5-difluorobenzenesulfonyl chloride and rac-4-methoxy-indane-1-ylamine (CAS 52372-96-0).

Example 41

(+)-N-{2-[(2,3-Dihydro-benzofuran-3-yl)amino]-quinolin-5-yl}-3,5-difluoro-benzenesulfonamide Rac-N-{2-[(2,3-Dihydro-benzofuran-3-yl)amino]-quinolin-5-yl}-3,5-difluoro-benzenesulfonamide (example 38) was separated on Chiralpak AD with 20% ethanol in heptane. The title compound was eluted as the second enantiomer.

Example 42

3,5-Difluoro-N-[2-((1R,2S)-2-hydroxy-indan-1-ylamino)-quinolin-5-yl]-benzenesulfonamide The title compound, MS: m/e=468.5 (M+H$^+$), was prepared in accordance with the general method of example 13 from 5-nitro-2-chloroquinoline, 3,5-difluorobenzenesulfonyl chloride and (1R,2S)-(+)-cis-1-amino-2-indanol.

Example 43

N5-(3H-Imidazol-4-ylmethyl)-N2-(R)-indan-1-yl-quinoline-2,5-diamine

Step A

5-Nitro-2-chloroquinoline (CAS 13067-94-2, 2.4 g, 11.5 mmol) and (R)-1-aminoindane (3.13 g, 23.5 mmol) were stirred in a sealed tube at 120° C. overnight. The reaction mixture was purified by flash chromatography on silica gel (cyclohexane/ethyl acetate 100:0->50:50 gradient). (R)-Indan-1-yl-(5-nitro-quinolin-2-yl)-amine was obtained as a brown solid (2.67 g, 76%), MS: m/e=306.2 (M+H$^+$).

Step B (R)-Indan-1-yl-(5-nitro-quinolin-2-yl)-amine (2.66 g, 8.72 mmol) was dissolved in 420 mL ethanol and palladium on charcoal (10%, 176 mg, 0.437 mmol) was added. He reaction mixture was hydrogenated with a hydrogen ballon at room temperature overnight and filtered. The fltrate was evaporated off. The crude (R)—N2-indan-1-yl-quinoline-2,5-diamine (2.29 g, 95%), MS: m/e=276.3 (M+H$^+$), was used without further purification for the next step.

Step C (R)—N2-Indan-1-yl-quinoline-2,5-diamine (150 mg, 0.545 mmol) was dissolved in 5 mL methanol. 4(5)-Formylimidazole (64 mg, 0.667 mmol) and acetic acid (98 mg, 1.63 mmol) were added. The reaction mixture was stirred at room temperature for 1 h. Sodium cyanoborohydride (90 mg, 1.43 mmol) was added and stirring was continued overnight. The reaction mixture was quenched by addition of 50 mL sat. sodium bicarbonate solution. The mixture was extracted three times with ethyl acetate (50 mL each). The organic phases ware pooled, dried with sodium sulfate, filtered and evaporated. The crude product was purified by flash chromatography on silica gel (dichloromethane/methanol/ammonia 100:0:0->90:10:1 gradient). The title compound was obtained as a yellow solid (128 mg, 66%), MS: m/e=356.1 (M+H$^+$).

Example 44

N2-(R)-Indan-1-yl-N5-(3-methyl-3H-imidazol-4-ylmethyl)-quinoline-2,5-diamine

The title compound, MS: m/e=370.1 (M+H$^+$), was prepared in accordance with the general method of example 43 from 5-nitro-2-chloroquinoline, (R)-1-aminoindane and 1-methyl-1H-imidazole-5-carbaldehyde.

Example 45

3,5-Difluoro-N-[2-((R)-indan-1-ylamino)-quinolin-5-yl]-benzamide

Step A

5-Nitro-2-chloroquinoline (CAS 13067-94-2, 2.4 g, 11.5 mmol) and (R)-1-aminoindane (3.13 g, 23.5 mmol) were stirred in a sealed tube at 120° C. overnight. The reaction mixture was purified by flash chromatography on silica gel (cyclohexane/ethyl acetate 100:0->50:50 gradient). (R)-Indan-1-yl-(5-nitro-quinolin-2-yl)-amine was obtained as a brown solid (2.67 g, 76%), MS: m/e=306.2 (M+H$^+$).

Step B (R)-Indan-1-yl-(5-nitro-quinolin-2-yl)-amine (2.66 g, 8.72 mmol) was dissolved in 420 mL ethanol and palladium on charcoal (10%, 176 mg, 0.437 mmol) was added. He reaction mixture was hydrogenated with a hydrogen ballon at room temperature overnight and filtered. The filtrate was evaporated off. The crude (R)—N2-indan-1-yl-quinoline-2,5-diamine (2.29 g, 95%), MS: m/e=276.3 (M+H$^+$), was used without further purification for the next step.

Step C (R)-Indan-1-yl-(5-nitro-quinolin-2-yl)-amine (0.15 g, 0.545 mmol) was dissolved in 1.5 mL pyridine and 3,5-difluorobenzoylchloride (0.98 g, 0.554 mmol) was added. The reaction mixture was stirred at room temperature overnight. 1 N HCl was added until pH5. The mixture was extracted three times with ethyl acetate (50 mL each). The organic phases ware pooled, dried with sodium sulfate, filtered and evaporated. The crude product was recrystallized from isopropanol and diisopropylether. The title compound was obtained as a brown solid (44 mg, 19%), MS: m/e=416.3 (M+H$^+$).

Example 46

4-(Cyclopropylmethyl-amino)-N-[2-((R)-indan-1-ylamino)-quinolin-5-yl]-benzenesulfonamide 4-Fluoro-N-[2-((R)-indan-1-ylamino)-quinolin-5-yl]-benzenesulfonamide (product example 1, 0.175 g, 0.404 mmol) was suspended in 2 mL cyclopropanemethylamine. The reaction mixture was stirred in a sealed tube at 120° C. overnight. The reaction mixture was purified by flash chromatography on silica gel (heptan/ethyl acetate 100:0->50:50 gradient). The title compound was obtained as a white solid (46 mg, 24%), MS: m/e=485.5 (M+H$^+$).

Example 47

1-Methyl-1H-imidazole-4-sulfonic acid [2-((R)-indan-1-ylamino)-quinolin-5-yl]-amide The title compound, MS: m/e=420.3 (M+H$^+$), was prepared in accordance with the general method of example 45 from 5-nitro-2-chloroquinoline, (R)-1-aminoindane and 1-methylimidazol-4-sulfonylchloride.

Example 48

N5-(5-Fluoro-pyridin-3-yl)-N2-(R)-indan-1-yl-quinoline-2,5-diamine (R)—N2-Indan-1-yl-quinoline-2,5-diamine (example 43, step A+B, 150 mg, 0.545 mmol) was dissolved in 3 mL dioxane. Argon was bubbled through the solution for 2 minutes to remove oxygen. 3-Bromo-5-fluoropyridine (195 mg, 1.11 mmol), sodium tert.-butylate (135 mg, 1.41 mmol), 1,1'-bis(diphenylphosphin)ferrocen (47 mg, 0.08 mmol) and 1,1'-bis(diphenylphosphin)ferrocen-palladium(II) chloride (22 mg, 0.03 mmol) were added. The reaction mixture was stirred in a sealed tube at 120° C. overnight. The solvent was evaporated and the residue purified by flash chromatography on silica gel (cyclohexane/ethyl acetate 100:0->50:50 gradient). The title compound was obtained as a light brown solid (147 mg, 73%), MS: m/e =371.4 (M+H$^+$).

Example 49

N5-(1H-Imidazol-2-ylmethyl)-N2-(R)-indan-1-yl-quinoline-2,5-diamine

The title compound, MS: m/e=356.4 (M+H$^+$), was prepared in accordance with the general method of example 43 from 5-nitro-2-chloroquinoline, (R)-1-aminoindane and imidazole-2-carbaldehyde.

Example 50

N2-(R)-Indan-1-yl-N5-(1H-pyrazol-3-ylmethyl)-quinoline-2,5-diamine

The title compound, MS: m/e=356.3 (M+H$^+$), was prepared in accordance with the general method of example 43 from 5-nitro-2-chloroquinoline, (R)-1-aminoindane and pyrazole-3-carbaldehyde.

Example 51

N-(2-Cyclohexylamino-quinolin-5-yl)-4-fluoro-benzenesulfonamide

The title compound, MS: m/e=400.3 (M+H$^+$), was prepared in accordance with the general method of example 13 from 5-nitro-2-chloroquinoline, 4-fluorobenzenesulfonyl chloride and cyclohexylamine.

Example 52

3,5-Difluoro-N-[2-((1S,2R)-2-hydroxy-indan-1-ylamino)-quinolin-5-yl]-benzenesulfonamide The title compound, MS: m/e=468.5 (M+H$^+$), was prepared in accordance with the general method of example 13 from 5-nitro-2-chloroquinoline, 3,5-difluorobenzenesulfonyl chloride and (1S,2R)-(−)-1-amino-2-indanol.

Example 53

2-(R)-Indan-1-yl-N5-(2-methyl-1H-imidazol-4-ylmethyl)-quinoline-2,5-diamine

The title compound, MS: m/e=370.4 (M+H$^+$), was prepared in accordance with the general method of example 43 from 5-nitro-2-chloroquinoline, (R)-1-aminoindane and 2-methyl-1H-imidazol-4-carbaldehyde.

Example 54

N-(2-Cycloheptylamino-quinolin-5-yl)-4-fluoro-benzenesulfonamide

The title compound, MS: m/e=414.3 (M+H$^+$), was prepared in accordance with the general method of example 13 from 5-nitro-2-chloroquinoline, 4-fluorobenzenesulfonyl chloride and cycloheptylamine.

Example 55

N2-(R)-Indan-1-yl-N5-(1-methyl-1H-pyrazol-4-ylmethyl)-quinoline-2,5-diamine

The title compound, MS: m/e=370.4 (M+H$^+$), was prepared in accordance with the general method of example 43 from 5-nitro-2-chloroquinoline, (R)-1-aminoindane and 1-methyl-1H-pyrazol-4-carbaldehyde.

Example 56

N2-(R)-Indan-1-yl-N5-(1H-indol-4-ylmethyl)-quinoline-2,5-diamine

The title compound, MS: m/e=405.5 (M+H$^+$), was prepared in accordance with the general method of example 43 from 5-nitro-2-chloroquinoline, (R)-1-aminoindane and indole-4-carbaldehyde.

Example 57 rac-N5-(1H-Indol-4-ylmethyl)-N2-(7-methoxy-indan-1-yl)-quinoline-2,5-diamine

The title compound, MS: m/e=435.4 (M+H$^+$), was prepared in accordance with the general method of example 43 from 5-nitro-2-chloroquinoline, rac-7-methoxy-indane-1-ylamine and indole-4-carbaldehyde.

Example 58

N5-(1H-Imidazol-4-ylmethyl)-N2-(7-methoxy-indan-1-yl)-quinoline-2,5-diamine

The title compound, MS: m/e=386.4 (M+H$^+$), was prepared in accordance with the general method of example 43 from 5-nitro-2-chloroquinoline, rac-7-methoxy-indane-1-ylamine and 4(5)-formylimidazole.

Example 59 rac 3,5-Difluoro-N-[2-(8-methoxy-1,2,3,4-tetrahydro-naphthalen-1-ylamino)-quinolin-5-yl]-benzenesulfonamide The title compound, MS: m/e=496.3 (M+H$^+$), was prepared in accordance with the general method of example 13 from 5-nitro-2-chloroquinoline, 3,5-difluorobenzenesulfonyl chloride and 8-methoxy-1,2,3,4-tetrahydronaphthalen-1-amine (CAS 535935-61-6).

Example 60 rac-exo-N-[2-(Bicyclo[2.2.1]hept-2-ylamino)-quinolin-5-yl]-4-fluoro-benzenesulfonamide The title compound, MS: m/e=412.5 (M+H$^+$), was prepared in accordance with the general method of example 13 from 5-nitro-2-chloroquinoline, 4-fluorobenzenesulfonyl chloride and exo-2-aminonorbornane.

Example 61 rac-1-Methyl-1H-indole-4-sulfonic acid [2-(7-methoxy-indan-1-ylamino)-quinolin-5-yl]-amide The title compound, MS: m/e=499.0 (M+H$^+$), was prepared in accordance with the general method of example 45 from 5-nitro-2-chloroquinoline, rac-7-methoxy-indane-1-ylamine and 1-methyl-1H-indole-4-sulfonylchloride.

Example 62 rac-3,5-Difluoro-N-[2-(1,2,3,4-tetrahydro-naphthalen-1-ylamino)-quinolin-5-yl]-benzenesulfonamide The title compound, MS: m/e=466.1 (M+H$^+$), was prepared in accordance with the general method of example 13 from 5-nitro-2-chloroquinoline, 3,5-difluorobenzenesulfonyl chloride and rac-1,2,3,4-tetrahydro-1-naphthylamine.

Example 63

(R)-Indan-1-yl-(5-phenyl-quinolin-2-yl)-amine

Step A
(R)-Indan-1-yl-(5-iodo-quinolin-2-yl)-amine was prepared from 5-iodo-2-chloroquinoline and (R)-1-aminoindane as described in example 6 step A.
Step B
(R)-Indan-1-yl-(5-iodo-quinolin-2-yl)-amine (150 mg, 0.39 mmol) was dissolved in 5 mL 1,2-dimethoxyethane and 2.5 mL 1M sodium carbonate solution. Phenylboronic acid (59 mg, 0.48 mmol) was added. Argon was bubbled through the solution for 2 minutes to remove oxygen. Triphenylphosphine (11 mg, 0.04 mmol) and Palladium acetate (4 mg, 0.02 mmol) were added. The reaction mixture was refluxed overnight. The reaction was diluted with 50 mL water and the mixture was extracted three times with ethyl acetate (100 mL each). The organic phases ware pooled, dried with sodium sulfate, filtered and evaporated. The residue was purified by flash chromatography on silica gel (heptane/ethyl acetate 100:0->80:20 gradient). The title compound was obtained as a colorless solid (114 mg, 87%), MS: m/e=337.4 (M+H$^+$).

Example 64

N5-[2-(2-Dimethylamino-ethoxy)-benzyl]-N2-(R)-indan-1-yl-quinoline-2,5-diamine

The title compound, MS: m/e=453.4 (M+H$^+$), was prepared in accordance with the general method of example 6 from 5-iodo-2-chloroquinoline, (R)-1-aminoindane and 2-[2-(dimethylamino)ethoxy]benzylamine.

Example 65

(R)-Indan-1-yl-(5-o-tolyl-quinolin-2-yl)-amine

The title compound, MS: m/e=351.5 (M+H$^+$), was prepared in accordance with the general method of example 63 from 5-iodo-2-chloroquinoline, (R)-1-aminoindane and ortho-tolylboronic acid.

Example 66

(R)-Indan-1-yl-(5-pyridin-3-yl-quinolin-2-yl)-amine

The title compound, MS: m/e=338.4 (M+H$^+$), was prepared in accordance with the general method of example 63 from 5-iodo-2-chloroquinoline, (R)-1-aminoindane and 3-pyridylboronic acid.

Example 67

Rac-N5-(3H-Imidazol-4-ylmethyl)-N2-(8-methoxy-1,2,3,4-tetrahydro-naphthalen-1-yl)-quinoline-2,5-diamine The title compound, MS: m/e=400.4 (M+H$^+$), was prepared in accordance with the general method of example 43 from 5-nitro-2-chloroquinoline, rac-8-methoxy-1,2,3,4-tetrahydronaphthalen-1-amine (CAS 535935-61-6) and 4(5)-formylimidazole.

Example 68

Rac-N2-(8-Methoxy-1,2,3,4-tetrahydro-naphthalen-1-yl)-N5-(1H-[1,2,3]triazol-4-ylmethyl)-quinoline-2,5-diamine The title compound, MS: m/e=401.5 (M+H$^+$), was prepared in accordance with the general method of example 43 from 5-nitro-2-chloroquinoline, rac-8-methoxy-1,2,3,4-tetrahydronaphthalen-1-amine (CAS 535935-61-6) and 1H-1,2,3-triazole-4-carbaldehyde.

Example 69

N2-(R)-Indan-1-yl-N5-(1H-indol-7-yl)-quinoline-2,5-diamine

The title compound, MS: m/e=391.1 (M+H$^+$), was prepared in accordance with the general method of example 6 from 5-iodo-2-chloroquinoline, (R)-1-aminoindane and 7-amino-indole.

Example 70

Rac-N5-(1H-Indol-4-ylmethyl)-N2-(8-methoxy-1,2,3,4-tetrahydro-naphthalen-1-yl)-quinoline-2,5-diamine The title compound, MS: m/e=449.3 (M+H$^+$), was prepared in accordance with the general method of example 43 from 5-nitro-2-chloroquinoline, rac-8-methoxy-1,2,3,4-tetrahydronaphthalen-1-amine (CAS 535935-61-6) and 4-formylindole.

Example 71

N2-(R)-Indan-1-yl-N5-(1H-indol-4-yl)-quinoline-2,5-diamine

The title compound, MS: m/e=391.3 (M+H$^+$), was prepared in accordance with the general method of example 6 from 5-iodo-2-chloroquinoline, (R)-1-aminoindane and 4-amino-indole.

Example 72

N2-(R)-Indan-1-yl-N5-(1H-indol-5-yl)-quinoline-2,5-diamine

The title compound, MS: m/e=391.3 (M+H$^+$), was prepared in accordance with the general method of example 6 from 5-iodo-2-chloroquinoline, (R)-1-aminoindane and 5-amino-indole.

Example 73

N2-(R)-Indan-1-yl-N5-(1H-indol-6-yl)-quinoline-2,5-diamine

The title compound, MS: m/e=391.4 (M+H$^+$), was prepared in accordance with the general method of example 6 from 5-iodo-2-chloroquinoline, (R)-1-aminoindane and 6-amino-indole.

Example 74

(R)-Indan-1-yl-[5-(1H-indol-4-yl)-quinolin-2-yl]-amine

The title compound, MS: m/e=376.5 (M+H$^+$), was prepared in accordance with the general method of example 63 from 5-iodo-2-chloroquinoline, (R)-1-aminoindane and 1H-indole-4-boronic acid.

Example 75

[5-(2-Chloro-phenyl)-quinolin-2-yl]-(R)-indan-1-yl-amine

The title compound, MS: m/e=371.0 (M+H$^+$), was prepared in accordance with the general method of example 63 from 5-iodo-2-chloroquinoline, (R)-1-aminoindane and 2-chlorophenyl-boronic acid.

Example 76

N5-(2,5-Dimethyl-2H-pyrazol-3-yl)-N2-(R)-indan-1-yl-quinoline-2,5-diamine

The title compound, MS: m/e=371.0 (M+H$^+$), was prepared in accordance with the general method of example 63 from 5-iodo-2-chloroquinoline, (R)-1-aminoindane and 2-chlorophenyl-boronic acid.

Example 77

N5-(4-Fluoro-phenyl)-N2-(R)-indan-1-yl-quinoline-2,5-diamine

The title compound, MS: m/e=370.0 (M+H$^+$), was prepared in accordance with the general method of example 48 from 5-nitro-2-chloroquinoline, (R)-1-aminoindane and 1-bromo-4-fluorobenzene.

Example 78

4-Fluoro-N-[2-((R)-indan-1-ylamino)-quinolin-5-yl]-benzamide

The title compound, MS: m/e=398.1 (M+H$^+$), was prepared in accordance with the general method of example 45 from 5-nitro-2-chloroquinoline, (R)-1-aminoindane and 4-fluorobenzoyl chloride.

Example 79

(R)-Indan-1-yl-[5-(5-methyl-[1,2,4]oxadiazol-3-yl)-quinolin-2-yl]-amine

Step A

A stirred suspension of 2-((R)-indan-1-ylamino)-quinoline-5-carbonitrile (example 80, step A) (571 mg, 2.0 mmol), hydroxylamine hydrochloride (514 mg, 7.4 mmol), sodium carbonate (424 mg, 4.0 mmol) in EtOH (7.5 ml) and water (7.5 ml) was heated under reflux conditions for 24 hours, water (40 ml) was added, and the mixture was extracted with ethyl acetate (3×75 ml). The combined organic layers were washed with brine (30 ml), dried (MgSO$_4$) and evaporated to yield the crude product as solid which was further purified by crystallization (dichloromethane/MeOH) to yield N-hydroxy-2-((R)-indan-1-ylamino)-quinoline-5-carboxamidine as white solid (500 mg, 79%).
MS: m/e=319.2 (M+H$^+$); m.p. 200.5° C.

Step B

To a stirred solution of acetic acid (127 mg, 2.12 mmol) in acetonitrile (8.5 ml) was added at room temperature 1-hydroxy-benzotriazole (403 mg, 2.98 mmol) and N-(3-dimethylaminopropyl)-N'-ethyl-carbodiimid-hydrochloride (465 mg, 2.43 mmol). The mixture was allowed to stir for 3 h at room temperature and N-hydroxy-2-((R)-indan-1-ylamino)-quinoline-5-carboxamidine (450 mg, 1.41 mmol) was added together with acetonitrile (7.5 ml). The mixture was allowed to stir for 2 h at room temperature, evaporated to dryness and diluted with acetic acid (14 ml). The reaction mixture was allowed to stir for 2 h at 100° C., evaporated, poured into saturated NaHCO$_3$ solution (50 ml) and extracted with ethyl acetate (3×80 ml). The combined organic layers were washed with brine (2×50 ml), dried (MgSO$_4$) and evaporated. The crude product was purified by flash chromatography (ethyl acetate/heptane) on silica gel and crystallization (ethyl acetate/heptane) to yield the title compound as light yellow solid (130 mg, 18%).
MS: m/e=343.2 (M+H$^+$)$^+$; m.p. 105° C.

Example 80

4-Fluoro-N-[2-((R)-indan-1-ylamino)-quinolin-5-ylmethyl]-benzamide

Step A

A mixture of (R)-indan-1-yl-(5-iodo-quinolin-2-yl)-amine (example 6, step A) (1.44 g, 3.73 mmol), zinc cyanide (482 mg, 4.1 mmol) and tetrakis-(triphenylphosphine)-palladium (431 mg, 0.37 mmol) in DMF (20 ml) was heated at 160° C. for 15 min in a microwave reactor. The reaction mixture was poured into water (50 ml) and extracted with ethyl acetate (2×100 ml). The combined organic layers were washed with brine (50 ml), dried (MgSO$_4$) and evaporated. The crude product was purified by flash chromatography (ethyl acetate/heptane) on silica gel and crystallization (diethyl ether/hexane) to yield 2-((R)-indan-1-ylamino)-quinoline-5-carbonitrile as light yellow solid (840 mg, 79%). M.p. 150° C.; MS: m/e=286.2 (M+H$^+$).

Step B

Hydrogenation of 2-((R)-indan-1-ylamino)-quinoline-5-carbonitrile (200 mg, 0.7 mmol) dissolved in methanol (10 ml) and 7N CH$_3$OH—NH$_3$ (5 ml) on Ra—Ni (200 mg) for 23 hours at room temperature yielded after removal of the catalyst by filtration and evaporation a yellow oil which was further purified by column chromatography (dichloromethane/MeOH/NH$_4$OH 15:1:0.1) on silica gel to yield (5-aminomethyl-quinolin-2-yl)-(R)-indan-1-yl-amine as light yellow oil (190 mg, 94%). MS: m/e=290.1 (M+H$^+$).
Step C To a cooled (ice bath) and stirred solution of (5-aminomethyl-quinolin-2-yl)-(R)-indan-1-yl-amine (100 mg, 0.345 mmol) and triethyl amine (38 mg, 0.38 mmol) in tetrahydrofuran (THF) (2 ml) was added 4-fluorobenzoyl chloride (60 mg, 0.38 mmol) and the mixture was allowed to stir at room temperature for 16 h. Evaporation and purification by flash chromatography (ethyl acetate/heptane) on silica gel yielded the title compound as white solid (90 mg, 63%). M.p. 145° C.; MS: m/e=412.3 (M+H$^+$).

Example 81

{5-[(4-Fluoro-benzylamino)-methyl]-quinolin-2-yl}-(R)-indan-1-yl-amine

A solution of (5-aminomethyl-quinolin-2-yl)-(R)-indan-1-yl-amine (example 80, step B) (200 mg, 0.69 mmol), 4-fluorobenzaldehyde (94 mg, 0.76 mmol) and acetic acid (166 mg, 2.76 mmol) in 1,1-dichloroethane (10 ml) was stirred at room temperature for 30 minutes. Afterwards sodium triacetoxyboron hydride (342 mg, 1.61 mmol) was added, the reaction mixture was allowed to stir for 17 hours at room temperature, poured into ice/saturated NaHCO$_3$ solution (20 ml) and extracted with ethyl acetate (3×50 ml). The combined organic layers were washed with brine (50 ml), dried (MgSO$_4$) and evaporated. The crude product was purified by flash chromatography (ethyl acetate/heptane) on silica gel to yield the title compound as light yellow oil (130 mg, 47%).
MS: m/e=398.3 (M+H$^+$).

Example 82

{5-[(4-Fluoro-phenyl)-imino-methyl]-quinolin-2-yl}-(R)-indan-1-yl-amine

To a cooled (ice bath) and stirred suspension of 2-((R)-indan-1-ylamino)-quinoline-5-carbonitrile (example 80, step A) (285 mg, 1.0 mmol) in THF (5 ml) was added drop wise a 1M solution of 4-fluorophenyl-magnesium bromide (6 ml, 6.0 mmol), the reaction mixture was heated under reflux conditions for 92 h and poured into ice-water (20 ml). 2N HCl (5 ml) was added, the mixture was stirred at room temperature for 10 min, 3 N NaOH (5 ml) was added and the mixture was extracted with ethyl acetate (3×80 ml). The combined organic layers were washed with brine (2×50 ml), dried (MgSO$_4$) and evaporated. The crude product was purified by flash chromatography (ethyl acetate/heptane) on silica gel to yield the title compound as light red foam (210 mg, 55%).
MS: m/e=382.2 (M+H$^+$).

Example 83

(4-Fluoro-phenyl)-[2-((R)-indan-1-ylamino)-quinolin-5-yl]-methanone

A mixture of {5-[(4-fluoro-phenyl)-imino-methyl]-quinolin-2-yl}-(R)-indan-1-yl-amine (example 81) (190 mg, 0.5 mmol), 2N HCl (6 ml) and THF (1.5 ml) was stirred at room temperature for 17 h, poured into saturated NaHCO$_3$ solution (40 ml) and extracted with ethyl acetate (2×50 ml). The combined organic layers were washed with brine (50 ml), dried (MgSO$_4$) and evaporated. The crude product was purified by flash chromatography (ethyl acetate/heptane) on silica gel to yield the title compound as light yellow foam (170 mg, 89%). MS: m/e 383.3 (M+H$^+$).

Example 84

[5-(Imino-phenyl-methyl)-quinolin-2-yl]-(R)-indan-1-yl-amine

The title compound, obtained as orange oil, MS: m/e=364.5 (M+H$^+$), was prepared in accordance with the general method of example 82 from 2-((R)-indan-1-ylamino)-quinoline-5-carbonitrile (example 80, step A) and phenyl-magnesium bromide.

Example 85

[2-((R)-Indan-1-ylamino)-quinolin-5-yl]-phenyl-methanone

The title compound, obtained as light yellow foam, MS: m/e=365.3 (M+H$^+$), was prepared in accordance with the general method of example 83 from [5-(imino-phenyl-methyl)-quinolin-2-yl]-(R)-indan-1-yl-amine (example 84).

Example 86

N-{2-[(1R)-2,3-dihydro-1H-inden-1-ylamino]quinolin-5-yl}-N'-(4-fluorophenyl)sulfamide (R)—N2-Indan-1-yl-quinoline-2,5-diamine (example 43, step A+B, 200 mg, 0.727 mmol) was dissolved in 3 mL pyridine and 4-fluoro-phenylsulfamoyl chloride (298 mg, 1.42 mmol) was added. The reaction mixture was stirred at 45° C. for 2 days and quenched by addition of 50 mL water. The mixture was extracted three times with ethyl acetate (50 mL each). The organic phases ware pooled, dried with sodium sulfate, filtered and evaporated. The residue was purified by flash chromatography on silica gel (heptane, tetrahydrofurane 100:0->50:50 gradient). The title compound was obtained as a brown solid (43 mg, 13%), MS: m/e=449.1 (M+H$^+$).

Example 87

N5-(3,5-Difluoro-benzyl)-N2-indan-2-yl-quinoline-2,5-diamine

The title compound, MS: m/e=402.4 (M+H$^+$), was prepared in accordance with the general method of example 43 from 5-nitro-2-chloroquinoline, 2-aminoindane and 3,5-difluorobenzaldehyde.

Example 88

N2-Indan-2-yl-N5-(1H-indol-4-ylmethyl)-quinoline-2,5-diamine

The title compound, MS: m/e=405.3 (M+H$^+$), was prepared in accordance with the general method of example 43 from 5-nitro-2-chloroquinoline, 2-aminoindane and 4-formylindane.

Example 89

(4-Fluoro-phenyl)-[2-((R)-indan-1-ylamino)-quinolin-5-yl]-methanone oxime

A stirred suspension of (4-fluoro-phenyl)-[2-((R)-indan-1-ylamino)-quinolin-5-yl]-methanone (example 83) (100 mg, 0.26 mmol), hydroxylamine hydrochloride (55 mg, 0.79 mmol) and sodium carbonate (83 mg, 0.78 mmol) in EtOH (2 ml) was heated under reflux conditions for 18 hours, the reaction mixture was poured into water (20 ml) and extracted with ethyl acetate (3×50 ml). The combined organic layers were washed with brine (50 ml), dried (MgSO$_4$) and evaporated. The crude product was further purified by flash chromatography on silica gel (heptane/ethyl acetate) and crystallization (diethyl ether/heptane) to yield the title compound as off-white solid (34 mg, 33%).

M.p. 184° C.; MS: m/e=398.3 (M+H$^+$).

Example 90

(4-Chloro-phenyl)-[2-((R)-indan-1-ylamino)-quinolin-5-yl]-methanone

The title compound, obtained as light yellow foam, MS: m/e=440.3 (M+H$^+$), was prepared in accordance with the general methods of examples 82 and 83 from 2-((R)-indan-1-ylamino)-quinoline-5-carbonitrile (example 80, step A) and 4-chlorophenyl-magnesium bromide.

Example 91

[2-((R)-Indan-1-ylamino)-quinolin-5-yl]-phenyl-methanone oxime

The title compound, obtained as white solid, m.p. 175.5° C.; MS: m/e=380.3 (M+H$^+$), was prepared in accordance with the general method of example 89 from [2-((R)-indan-1-ylamino)-quinolin-5-yl]-phenyl-methanone (example 85) and hydroxylamine hydrochloride.

Example 92

(4-Chloro-phenyl)-[2-((R)-indan-1-ylamino)-quinolin-5-yl]-methanone oxime

The title compound, obtained as white solid, m.p. 194° C.; MS: m/e=414.2 (M+H$^+$), was prepared in accordance with the general method of example 89 from (4-chloro-phenyl)-[2-((R)-indan-1-ylamino)-quinolin-5-yl]-methanone (example 90) and hydroxylamine hydrochloride.

Example 93

[2-((R)-Indan-1-ylamino)-(4-methoxy-phenyl)-quinolin-5-yl]-methanone

The title compound, obtained as orange oil, MS: m/e=395.2 (M+H$^+$), was prepared in accordance with the general methods of examples 82 and 83 from 2-((R)-indan-1-ylamino)-quinoline-5-carbonitrile (example 80, step A) and 4-methoxyphenyl-magnesium bromide.

Example 94

(3-Fluoro-phenyl)-[2-((R)-indan-1-ylamino)-quinolin-5-yl]-methanone

The title compound, obtained as light yellow oil, MS: m/e=383.3 (M+H$^+$), was prepared in accordance with the general methods of examples 82 and 83 from 2-((R)-indan-1-ylamino)-quinoline-5-carbonitrile (example 80, step A) and 3-fluorophenyl-magnesium bromide.

Example 95

[2-((R)-Indan-1-ylamino)-(4-methoxy-phenyl)-quinolin-5-yl]-methanone oxime

The title compound, obtained as off-white solid, m.p. 170° C.; MS: m/e=410.3 (M+H$^+$), was prepared in accordance with the general method of example 89 from [2-((R)-indan-1-ylamino)-(4-methoxy-phenyl)-quinolin-5-yl]-methanone (example 93) and hydroxylamine hydrochloride.

Example 96

(3-Fluoro-phenyl)-[2-((R)-indan-1-ylamino)-quinolin-5-yl]-methanone oxime

The title compound, obtained as white solid, m.p. 179.5° C.; MS: m/e=398.2 (M+H$^+$), was prepared in accordance with the general method of example 89 from (3-fluoro-phenyl)-[2-((R)-indan-1-ylamino)-quinolin-5-yl]-methanone (example 94) and hydroxylamine hydrochloride.

Example 97

[2-((R)-Indan-1-ylamino)-(4-methyl-phenyl)-quinolin-5-yl]-methanone

The title compound, obtained as light yellow foam, MS: m/e=379.3 (M+H$^+$), was prepared in accordance with the general methods of examples 82 and 83 from 2-((R)-indan-1-ylamino)-quinoline-5-carbonitrile (example 80, step A) and 4-methylphenyl-magnesium bromide.

Example 98

[2-((R)-Indan-1-ylamino)-(4-methyl-phenyl)-quinolin-5-yl]-methanone O-methyl-oxime The title compound, obtained as light yellow oil, MS: m/e=408.4 (M+H$^+$), was prepared in accordance with the general method of example 89 from [2-((R)-indan-1-ylamino)-(4-methyl-phenyl)-quinolin-5-yl]-methanone (example 97) and O-methyl-hydroxylamine hydrochloride.

Example 99

[2-((R)-Indan-1-ylamino)-(4-methyl-phenyl)-quinolin-5-yl]-methanone oxime

The title compound, obtained as off-white solid, m.p. 180° C.; MS: m/e=394.2 (M+H$^+$), was prepared in accordance with the general method of example 89 from [2-((R)-indan-1-ylamino)-(4-methyl-phenyl)-quinolin-5-yl]-methanone (example 97) and hydroxylamine hydrochloride.

Example 100

(3,5-Difluoro-phenyl)-[2-((R)-indan-1-ylamino)-quinolin-5-yl]-methanone

The title compound, obtained as yellow foam, MS: m/e=401.3 (M+H$^+$), was prepared in accordance with the general methods of examples 82 and 83 from 2-((R)-indan-1-ylamino)-quinoline-5-carbonitrile (example 80, step A) and 3,5-difluorophenyl-magnesium bromide.

Example 101

(3,5-Difluoro-phenyl)-[2-((R)-indan-1-ylamino)-quinolin-5-yl]-methanone oxime

The title compound, obtained as light yellow solid, m.p. 120.5° C.; MS: m/e=416.4 (M+H$^+$), was prepared in accordance with the general method of example 89 from (3,5-difluoro-phenyl)-[2-((R)-indan-1-ylamino)-quinolin-5-yl]-methanone (example 100) and hydroxylamine hydrochloride.

Example 102

[2-((R)-Indan-1-ylamino)-quinolin-5-yl]-thiophen-2-yl-methanone

The title compound, obtained as light yellow solid, MS: m/e=371.3 (M+H$^+$); m.p. 176° C., was prepared in accordance with the general methods of examples 82 and 83 from 2-((R)-indan-1-ylamino)-quinoline-5-carbonitrile (example 80, step A) and thiophen-2-yl-magnesium bromide.

Example 103

[2-((R)-Indan-1-ylamino)-quinolin-5-yl]-(4-morpholin-4-ylmethyl-phenyl)-methanone The title compound, obtained as yellow solid, MS: m/e=464.3 (M+H$^+$); m.p. 160° C., was prepared in accordance with the general methods of examples 82 and 83 from 2-((R)-indan-1-ylamino)-quinoline-5-carbonitrile (example 80, step A) and [4-(4-morpholinyl-methyl)-phenyl]-magnesium bromide.

Example 104

[2-((R)-Indan-1-ylamino)-quinolin-5-yl]-thiophen-2-yl-methanone oxime

The title compound, obtained as off-white solid, m.p. 194° C.; MS: m/e=386.3 (M+H$^+$); m.p. 180.5° C., was prepared in accordance with the general method of example 89 from [2-((R)-indan-1-ylamino)-quinolin-5-yl]-thiophen-2-yl-methanone (example 102) and hydroxylamine hydrochloride.

Example 105

[2-((R)-Indan-1-ylamino)-quinolin-5-yl]-(4-morpholin-4-ylmethyl-phenyl)-methanone oxime The title compound, obtained as white solid, m.p. 167° C.; MS: m/e=479.1 (M+H$^+$); m.p. 180.5° C., was prepared in accordance with the general method of example 89 from [2-((R)-indan-1-ylamino)-quinolin-5-yl]-(4-morpholin-4-ylmethyl-phenyl)-methanone (example 103) and hydroxylamine hydrochloride.

Synthesis of Intermediates

Example A rac-7-Methoxy-indane-1-ylamine

Step A

7-Methoxy-indan-1-one (CAS 34985-41-6, 5.0 g, 31 mmol) was dissolved in 25 mL ethanole. Hydroxylamine hydrochloride (4.39 g, 63 mmol) and sodium acetate (5.21 g, 82 mmol) was added and the mixture was refluxed for 2 h. The reaction mixture was poured into 30 mL water, the solid was filtered off and washed with water and dried. The crude 7-methoxy-indan-1-one oxime (5.1 g, 93%, MS: m/e=178.3 (M+H$^+$)) was used without further purification for the next step.

Step B

7-Methoxy-indan-1-one oxime (5 g, 28 mmol) was suspended in 250 mL methanol. Palladium on charcoal (10%, 0.3 g) was added and the reaction was hydrogenated with a hydrogen ballon for 5 days. Palladium on charcoal was filtered off and the filtrate was evaporated. The title compound was obtained as a yellow liquid (1.89, 41%) and used without any further purification for the next step.

Example 106

Test Description

A [$^3$H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM MgCl$_2$ (pH 7.4) and 10 μM pargyline. The binding assay was carried out in 96-well-plates in the presence of [$^3$H]LSD (approximately 1 nM), approximately 2 μg/well of membrane protein, and 0.5 mg of Ysi-poly-1-lysine SPA beads in a final volume of 200 μl of buffer. Non-specific binding was defined using methiothepin 2 μM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. IC$_{50}$ values were calculated using a non-linear curve fitting program and K$_i$ values calculated using the Cheng-Prussoff equation.

The activity of the compounds according to the invention is exemplified in the table below:

| Compound of Example | Ki (μM) |
|---|---|
| 1 | 0.00376 |
| 4 | 0.03731 |
| 5 | 0.00362 |
| 6 | 0.00185 |
| 7 | 0.00284 |
| 8 | 0.0135 |
| 9 | 0.09091 |
| 11 | 0.00586 |
| 12 | 0.00513 |
| 16 | 0.01115 |
| 17 | 0.00924 |
| 18 | 0.02212 |
| 19 | 0.00718 |
| 20 | 0.01807 |
| 21 | 0.01582 |
| 23 | 0.02349 |
| 27 | 0.02579 |
| 28 | 0.00423 |
| 29 | 0.00972 |
| 30 | 0.01901 |
| 32 | 0.0127 |
| 33 | 0.01205 |
| 35 | 0.00781 |

-continued

| Compound of Example | Ki (μM) |
|---|---|
| 37 | 0.01776 |
| 39 | 0.00457 |
| 41 | 0.02294 |
| 43 | 0.00645 |
| 45 | 0.0977 |
| 49 | 0.02251 |
| 50 | 0.01361 |
| 53 | 0.00757 |
| 55 | 0.02555 |
| 56 | 0.00165 |
| 57 | 0.0037 |
| 58 | 0.00236 |
| 59 | 0.01341 |
| 60 | 0.19702 |
| 61 | 0.00466 |
| 62 | 0.06074 |
| 63 | 0.22943 |
| 64 | 0.00603 |
| 65 | 0.17312 |
| 66 | 0.31965 |
| 67 | 0.0105 |
| 68 | 0.01532 |
| 69 | 0.00561 |
| 70 | 0.01586 |
| 71 | 0.00294 |
| 72 | 0.006 |
| 73 | 0.0047 |
| 74 | 0.04166 |
| 75 | 0.12747 |
| 76 | 0.033 |
| 77 | 0.00638 |
| 78 | 0.0916 |
| 79 | 0.13432 |
| 80 | 0.03442 |
| 81 | 0.15078 |
| 82 | 0.00782 |
| 83 | 0.01153 |
| 84 | 0.0171 |
| 85 | 0.02408 |
| 86 | 0.01002 |
| 87 | 0.05616 |
| 88 | 0.04433 |
| 89 | 0.0023 |
| 90 | 0.0497 |
| 91 | 0.00155 |
| 92 | 0.00548 |
| 93 | 0.0158 |
| 94 | 0.1175 |
| 95 | 0.00411 |
| 96 | 0.00122 |
| 97 | 0.0374 |
| 98 | 0.0498 |
| 99 | 0.0018 |
| 100 | 0.264 |
| 101 | 0.0077 |
| 102 | 0.0334 |
| 103 | 0.678 |
| 104 | 0.00364 |
| 105 | 0.0232 |

Example 107

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 3 |
| 4. | Macrocrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example 108

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of general formula (I),

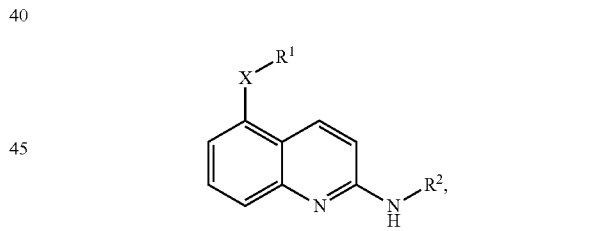

wherein
X is selected from the group consisting of a bond, —$NR^a$—, —O—, —S—, —$SO_2$—, —$NR^b$—$S(O)_2$—, —$NR^c$—$CH_2$—, —$OCH_2$—, —$CH_2O$—, —$SCH_2$—, —$CH_2S$—, —$NR^d$—, —C(O)—, —$CH_2$—$NR^c$—, —$CH_2CH_2$—, —CH=CH—, —$CH_2$—$S(O)_2$—, —$OCH_2CH_2$—, —$SCH_2CH_2$—, —$NR^cCH_2CH_2$—, —$CH_2$—$NR^d$—C(O)—, —$CH_2$—$NR^c$—$CH_2$—, —C($NR^k$)—, —C(O)—, —$NR^b$—$S(O)_2$—$NR^b$—, and —C(N—$OR^p$)—;
$R^1$ is mono- or bicyclic aryl, or mono- or bicyclic heteroaryl, each optionally substituted by one or more substituents independently selected from the group consisting of:
halo,
alkyl, optionally substituted by —OH or —CN,
alkoxy,
—$S(O)_2$-alkyl, —NR$^e$R$^f$,
—S(O)$_2$—NR$^g$R$^h$,
haloalkyl,
—CH$_2$—O-alkyl,
—(OCH$_2$CH$_2$)$_m$—OR$^i$, wherein m is an integer from 1 to 3,
—(OCH$_2$CH$_2$)$_m$—NR$^q$R$^r$, wherein m is an integer from 1 to 3,
—CH$_2$—(N-morpholino),
—CH$_2$—(OCH$_2$CH$_2$)$_m$—OR$^j$, wherein m is an integer from 1 to 3,
hydroxy,
cyano,
nitro, and
allyl;
R$^2$ is 5- to 7-membered cycloalkyl or heterocycloalkyl, or bicyclo[2.2.1]heptyl each optionally anellated with an aromatic 5- or 6-membered carbo- or heterocycle, each ring optionally and independently substituted with one or more substituents independently selected from the group consisting of:
alkoxy,
hydroxy,
halo,
alkyl, optionally substituted by —OH or —CN,
—S(O)$_2$-alkyl,
—NR$^e$R$^f$,
—S(O)$_2$—NR$^g$R$^h$,
—CH$_2$—O-alkyl,
—(OCH$_2$CH$_2$)$_m$—OR$^i$, wherein m is an integer from 1 to 3,
—CH$_2$—(OCH$_2$CH$_2$)$_m$—OR$^j$, wherein m is an integer from 1 to 3,
cyano,
nitro, and
allyl;
R$^a$, R$^b$, R$^c$, R$^d$, R$^e$, R$^f$, R$^g$, R$^h$, R$^i$, R$^j$, R$^k$, R$^p$, R$^q$ and R$^r$ are each independently selected from the group consisting of: hydrogen, alkyl and —(CH$_2$)$_n$-cycloalkyl, wherein n is an integer from 0 to 3;
or a pharmaceutically-acceptable-acid addition salt thereof.

2. A compound according to claim 1
wherein
X is selected from the group consisting of: a bond, —NR$^a$—, —O—, —S—, —SO$_2$—, —NR$^b$—S(O)$_2$—, —NR$^c$—CH$_2$—, —OCH$_2$—, —CH$_2$O—, —SCH$_2$—, —CH$_2$S—, —NR$^d$—, —C(O)—, —CH$_2$—NR$^e$—, —CH$_2$CH$_2$—, —CH=CH—, —CH$_2$—S(O)$_2$—, —OCH$_2$CH$_2$—, —SCH$_2$CH$_2$—, and —NR$^c$CH$_2$CH$_2$—;
R$^1$ is mono- or bicyclic aryl, or mono- or bicyclic heteroaryl, each optionally substituted by one or more substituents independently selected from the group consisting of:
halo,
alkyl, optionally substituted by —OH or —CN,
alkoxy,
—S(O)$_2$-alkyl,
—NR$^e$R$^f$,
—S(O)$_2$—NR$^g$R$^h$,
haloalkyl,
—CH$_2$—O-alkyl,
—(OCH$_2$CH$_2$)$_m$—OR$^i$, wherein m is an integer from 1 to 3,
—CH$_2$—(OCH$_2$CH$_2$)$_m$—OR$^j$, wherein m is an integer from 1 to 3,
hydroxy,
cyano,
nitro, and
allyl;
R$^2$ is 5- to 7-membered cycloalkyl or heterocycloalkyl, optionally anellated with an aromatic 5- or 6-membered carbo- or heterocycle, each ring optionally and independently substituted with one or more substituents independently selected from the group consisting of:
alkoxy,
hydroxy,
halo,
alkyl, optionally substituted by —OH or —CN,
—S(O)$_2$-alkyl,
—NR$^e$R$^f$,
—S(O)$_2$—NR$^g$R$^h$,
—CH$_2$—O-alkyl,
—(OCH$_2$CH$_2$)$_m$,—OR$^i$ wherein m is an integer from 1 to 3,
—CH$_2$—(OCH$_2$CH$_2$)$_m$—OR$^j$, wherein m is an integer from 1 to 3,
cyano,
nitro, and
allyl;
R$^a$, R$^b$, R$^c$, R$^d$, R$^e$, R$^f$, R$^g$, R$^h$, R$^i$ and R$^j$ are each independently selected from the group consisting of hydrogen, alkyl and —(CH$_2$)$_n$-cycloalkyl, wherein n is an integer from 0 to 3;
or a pharmaceutically-acceptable acid-addition salt thereof.

3. A compound according to claim 1, wherein
X is selected from the group consisting of —NR$^a$—, —O—, —NR$^b$—S(O)$_2$—, —NR$^c$—CH$_2$—, —OCH$_2$—, and —NR$^d$—C(O)—; and
R$^a$, R$^b$, R$^c$ and R$^d$ are each independently hydrogen or alkyl.

4. A compound according to claim 1, wherein
R$^1$ is mono- or bicyclic aryl, or mono- or bicyclic heteroaryl, each optionally substituted by one or more substituents independently selected from the group consisting of:
halo,
alkyl, optionally substituted by OH,
alkoxy,
—S(O)$_2$-alkyl,
—NR$^e$R$^f$,
—S(O)$_2$—NR$^g$R$^h$,
haloalkyl,
—CH$_2$—O-alkyl,
—(OCH$_2$CH$_2$)$_m$—OR$^i$, wherein m is 1, and
—CH$_2$—(OCH$_2$CH$_2$)$_m$—OR$^j$, wherein m is 1; and
R$^e$, R$^f$, R$^g$, R$^h$, R$^i$ and R$^j$ are each independently selected from the group consisting of hydrogen, alkyl and —(CH$_2$)$_n$-cycloalkyl, wherein n is from 0 to 3.

5. A compound according to claim 1, wherein
R$^1$ is mono- or bicyclic aryl, or mono- or bicyclic heteroaryl, each optionally substituted by one or more substituents independently selected from the group consisting of:
halo,
alkyl,
alkoxy, and
—S(O)$_2$-alkyl, or —NR$^e$R$^f$; and
R$^e$, and R$^f$ are each independently selected from the group consisting of hydrogen, alkyl and —(CH$_2$)$_n$-cycloalkyl, wherein n is an integer from 0 to 3.

6. A compound according to claim 1, wherein
R$^1$ is selected from the group consisting of: optionally substituted phenyl, optionally substituted indolyl, optionally substituted imidazolyl, optionally substituted thienyl, optionally substituted pyridyl, and optionally substituted pyrazolyl.

7. A compound according to claim 1, wherein
$R^2$ is 5- to 7-membered cycloalkyl or heterocycloalkyl, optionally anellated with an aromatic 5- or 6-membered carbo- or heterocycle, each ring optionally and independently substituted with one or more substituents independently selected from the group consisting of:
alkoxy,
hydroxy,
halo, and
alkyl.

8. A compound according to claim 1, wherein
$R^2$ is selected from the group consisting of: cyclopentyl, cyclohexyl, cycloheptyl, tetrahydrofuran-3-yl, and tetrahydropyran-4-yl, optionally anellated with a benzo ring, each ring optionally and independently substituted with one or more substituents independently selected from the group consisting of:
alkoxy,
hydroxy,
halo, and
alkyl.

9. A compound according to claim 1, wherein X is —NH($SO_2$)— and the compound is selected from the group consisting of:
4-Fluoro-N-[2-((R)-indan-1-ylamino)-quinolin-5-yl]-benzenesulfonamide,
5-Chloro-thiophene-2-sulfonic acid [2-((R)-indan-1-ylamino)-quinolin-5-yl]-amide,
3,5-Difluoro-N-[2-((R)-indan-1-ylamino)-quinolin-5-yl]-benzenesulfonamide,
3,4,5-Trifluoro-N-[2-((R)-indan-1-ylamino)-quinolin-5-yl]-benzenesulfonamide,
rac-3,4,5-Trifluoro-N-[2-(7-methoxy-indan-1-ylamino)-quinolin-5-yl]-benzenesulfonamide,
(+)-3,4,5-Trifluoro-N-[2-(6-methoxy-indan-1-ylamino)-quinolin-5-yl]-benzenesulfonamide,
rac-4-Fluoro-N-[2-(6-methoxy-indan-1-ylamino)-quinolin-5-yl]-benzenesulfonamide,
rac-4-Fluoro-N-[2-(7-methoxy-indan-1-ylamino)-quinolin-5-yl]-benzenesulfonamide,
(+)-4-Fluoro-N-[2-(6-methoxy-indan-1-ylamino)-quinolin-5-yl]-benzenesulfonamide,
3,5-Difluoro-N-[2-(7-methoxy-indan-1-ylamino)-quinolin-5-yl]-benzenesulfonamide,
(+)-N-{2-[(2,3-Dihydro-benzofuran-3-yl)amino]-quinolin-5-yl}-3,5-difluoro-benzenesulfonamide,
rac-exo-N-[2-(Bicyclo[2.2.1]hept-2-ylamino)-quinolin-5-yl]-4-fluoro-benzenesulfonamide,
rac-1-Methyl-1H-indole-4-sulfonic acid-2-(7-methoxy-indan-1-ylamino)-quinolin-5-yl]-amide,
rac-3,5-Difluoro-N-[2-(1,2,3,4-tetrahydro-naphthalen-1-ylamino)-quinolin-5-yl]-benzenesulfonamide,
and pharmaceutically-acceptable acid-addition salts thereof.

10. A compound according to claim 1, wherein X is —OCH₂— and the compound is selected from the group consisting of:
(R)-Indan-1-yl-[5-(pyridin-3-ylmethoxy)-quinolin-2-yl]-amine,
and pharmaceutically-acceptable acid-addition salts thereof.

11. A compound according to claim 1, wherein X is —NHCH₂— and the compound is selected from the group consisting of:
N5-(3,5-Difluoro-benzyl)-N2-(R)-indan-1-yl-quinoline-2,5-diamine,
N2-(R)-Indan-1-yl-N5-pyridin-3-ylmethyl-quinoline-2,5-diamine,
rac-N5-(3,5-Difluoro-benzyl)-N2-(2,3-dihydro-benzofuran-3-yl)-quinoline-2,5-diamine,
rac-N2-(2,3-Dihydro-benzofuran-3-yl)-N5-pyridin-3-ylmethyl-quinoline-2,5-diamine,
rac-N2-(6-Methoxy-indan-1-yl)-N5-pyridin-3-ylmethyl-quinoline-2,5-diamine,
(+)-N2-2,3-Dihydro-benzofuran-3-yl-N5-pyridin-3-ylmethyl-quinoline-2,5-diamine,
rac-N5-(3,5-Difluoro-benzyl)-N2-(6-methoxy-indan-1-yl)-quinoline-2,5-diamine,
(+)-N5-(3-Methanesulfonyl-benzyl)-N2-(6-methoxy-indan-1-yl)-quinoline-2,5-diamine,
(+)-N5-(3,5-Difluoro-benzyl)-2,3-dihydro-benzofuran-3-yl-quinoline-2,5-diamine,
(+)-N5-(3,5-Difluoro-benzyl)-N2-(6-methoxy-indan-1-yl)-quinoline-2,5-diamine,
(+)-N2-(6-Methoxy-indan-1-yl)-N5-pyridin-3-ylmethyl-quinoline-2,5-diamine,
N5-[2-(2-Dimethylamino-ethoxy)-benzyl]-N2-(R)-indan-1-yl-quinoline-2,5-diamine,
rac-N5-(3H-Imidazol-4-ylmethyl)-N2-(8-methoxy-1,2,3,4-tetrahydro-naphthalen-1-yl)-quinoline-2,5-diamine,
rac-N2-(8-Methoxy-1,2,3,4-tetrahydro-naphthalen-1-yl)-N5-(1H-[1,2,3]triazol-4-ylmethyl)-quinoline-2,5-diamine,
Rac-N5-(1H-Indol-4-ylmethyl)-N2-(8-methoxy-1,2,3,4-tetrahydro-naphthalen-1-yl)-quinoline-2,5-diamine,
N5-(3,5-Difluoro-benzyl)-N2-indan-2-yl-quinoline-2,5-diamine,
N2-Indan-2-yl-N5-(11H-indol-4-ylmethyl)-quinoline-2,5-diamine,
and pharmaceutically-acceptable acid-addition salts thereof.

12. A compound according to claim 1 wherein X is —NH— and the compound is selected from the group consisting of:
N5-(4-Chloro-phenyl)-N2-(R)-indan-1-yl-quinoline-2,5-diamine,
N2-(R)-Indan-1-yl-N5-(1H-indol-7-yl)-quinoline-2,5-diamine,
N2-(R)-Indan-1-yl-N5-(1H-indol-4-yl)-quinoline-2,5-diamine,
N2-(R)-Indan-1-yl-N5-(1H-indol-5-yl)-quinoline-2,5-diamine,
N2-(R)-Indan-1-yl-N5-(1H-indol-6-yl)-quinoline-2,5-diamine,
N5-(2,5-Dimethyl-2H-pyrazol-3-yl)-N2-(R)-indan-1-yl-quinoline-2,5-diamine,
N5-(4-Fluoro-phenyl)-N2-(R)-indan-1-yl-quinoline-2,5-diamine,
and pharmaceutically-acceptable acid-addition salts thereof.

13. A compound according to claim 1 wherein X is —NCH₃SO₂— and the compound is selected from the group consisting of:
4-Fluoro-N-[2-((R)-indan-1-ylamino)-quinolin-5-yl]-N-methyl-benzenesulfonamide,
and pharmaceutically-acceptable acid-addition salts thereof.

14. A compound according to claim 1 wherein X is —O— and the compound is selected from the group consisting of:
[5-(4-fluoro-phenoxy)-quinolin-2-yl]-(R)-indan-1-yl-amine,
and pharmaceutically-acceptable acid-addition salts thereof.

15. A compound according to claim 1 wherein X is —NH(CO)— and the compound is selected from the group consisting of:
   3,5-difluoro-N-[2-((R)-indan-1-ylamino)-quinolin-5-yl]-benzamide,
   4-Fluoro-N-[2-((R)-indan-1-ylamino)-quinolin-5-ylmethyl]-benzamide,
and pharmaceutically-acceptable acid-addition salts thereof.

16. A compound according to claim 1 wherein X is —C(N—OH)— and the compound is selected from the group consisting of:
   (4-Fluoro-phenyl)-[2-((R)-indan-1-ylamino)-quinolin-5-yl]-methanone oxime,
   [2-((R)-Indan-1-ylamino)-quinolin-5-yl]-phenyl-methanone oxime,
   (4-Chloro-phenyl)-[2-((R)-indan-1-ylamino)-quinolin-5-yl]-methanone oxime,
   [2-((R)-Indan-1-ylamino)-(4-methoxy-phenyl)-quinolin-5-yl]-methanone oxime,
   (3-Fluoro-phenyl)-[2-((R)-indan-1-ylamino)-quinolin-5-yl]-methanone oxime,
   [2-((R)-Indan-1-ylamino)-(4-methyl-phenyl)-quinolin-5-yl]-methanone O-methyl-oxime,
   [2-((R)-Indan-1-ylamino)-(4-methyl-phenyl)-quinolin-5-yl]-methanone oxime,
   (3,5-Difluoro-phenyl)-[2-((R)-indan-1-ylamino)-quinolin-5-yl]-methanone oxime,
   [2-((R)-Indan-1-ylamino)-quinolin-5-yl]-thiophen-2-yl-methanone oxime,
   [2-((R)-Indan-1-ylamino)-quinolin-5-yl]-(4-morpholin-4-ylmethyl-phenyl)-methanone oxime,
and pharmaceutically-acceptable acid-addition salts thereof.

17. A compound according to claim 1 wherein X is —C(NH)— and the compound is selected from the group consisting of:
   {5-[(4-Fluoro-phenyl)-imino-methyl]-quinolin-2-yl}-(R)-indan-1-yl-amine,
   [5-(Imino-phenyl-methyl)-quinolin-2-yl]-(R)-indan-1-yl-amine,
and pharmaceutically-acceptable acid-addition salts thereof.

18. A compound according to claim 1 wherein X is —C(O)— and the compound is selected from the group consisting of:
   (4-Chloro-phenyl)-[2-((R)-indan-1-ylamino)-quinolin-5-yl]-methanone,
   [2-((R)-Indan-1-ylamino)-(4-methoxy-phenyl)-quinolin-5-yl]-methanone,
   (3-Fluoro-phenyl)-[2-((R)-indan-1-ylamino)-quinolin-5-yl]-methanone,
   [2-((R)-Indan-1-ylamino)-(4-methyl-phenyl)-quinolin-5-yl]-methanone,
   (3,5-Difluoro-phenyl)-[2-((R)-indan-1-ylamino)-quinolin-5-yl]-methanone,
   [2-((R)-Indan-1-ylamino)-quinolin-5-yl]-thiophen-2-yl-methanone,
   [2-((R)-Indan-1-ylamino)-quinolin-5-yl]-(4-morpholin-4-ylmethyl-phenyl)-methanone,
and pharmaceutically-acceptable acid-addition salts thereof.

19. A compound according to claim 1 wherein said compound is selected from the group consisting of:
   (R)-Indan-1-yl-(5-phenyl-quinolin-2-yl)-amine,
   (R)-Indan-1-yl-(5-pyridin-3-yl-quinolin-2-yl)-amine,
   (R)-Indan-1-yl-[5-(1H-indol-4-yl)-quinolin-2-yl]-amine,
   [5-(2-Chloro-phenyl)-quinolin-2-yl]-(R)-indan-1-yl-amine,
   (R)-Indan-1-yl-[5-(5-methyl-[1,2,4]oxadiazol-3-yl)-quinolin-2-yl]-amine,
   {5-[(4-Fluoro-benzylamino)-methyl]-quinolin-2-yl}-(R)-indan-1-yl-amine,
   N-{2-[(JR)-2,3-dihydro-1H-inden-1-ylamino]quinolin-5-yl}-N'-(4-fluorophenyl)sulfamide,
and pharmaceutically-acceptable acid-addition salts thereof.

20. A compound according to claim 1 selected from the group consisting of:
   [5-(4-Fluoro-benzyloxy)-quinolin-2-yl]-(R)-indan-1-yl-amine;
   (R)-Indan-1-yl-[5-(3-methoxy-benzyloxy)-quinolin-2-yl]-amine;
   N-[2-(Chroman-4-ylamino)-quinolin-5-yl]-3,5-difluoro-benzenesulfonamide;
   rac-N-[2-(2,3-Dihydro-benzofuran-3-ylamino)-quinolin-5-yl]-3,4,5-trifluoro-benzenesulfonamide;
   3,4,5-Trifluoro-N-[2-(indan-2-ylamino)-quinolin-5-yl]-benzenesulfonamide;
   rac-3,4,5-Trifluoro-N-[2-(6-methoxy-indan-1-ylamino)-quinolin-5-yl]-benzenesulfonamide;
   rac-N-[2-(2,3-Dihydro-benzofuran-3-ylamino)-quinolin-5-yl]-4-fluoro-benzenesulfonamide;
   rac-N5-(3-Methanesulfonyl-benzyl)-N2-(6-methoxy-indan-1-yl)-quinoline-2,5-diamine;
   rac-N5-(3-Methanesulfonyl-phenyl)-N2-(6-methoxy-indan-1-yl)-quinoline-2,5-diamine;
   N-(2-Cyclopentylamino-quinolin-5-yl)-4-fluoro-benzenesulfonamide;
   (+)-N5-(3-Methanesulfonyl-phenyl)-N2-(6-methoxy-indan-1-yl)-quinoline-2,5-diamine;
   N-[2-(5,8-Dimethoxy-1,2,3,4-tetrahydro-naphthalen-1-ylamino)-quinolin-5-yl]-4-fluoro-benzenesulfonamide;
   (+)-N-{2-[(2,3-Dihydro-benzofuran-3-yl)amino]-quinolin-5-yl}-4-fluoro-benzenesulfonamide;
   N-[2-(2,3-Dihydro-benzofuran-3-ylamino)-quinolin-5-yl]-3,5-difluoro-benzenesulfonamide;
   3,5-Difluoro-N-[2-(4-methoxy-indan-1-ylamino)-quinolin-5-yl]-benzenesulfonamide;
   3,5-Difluoro-N-[2-((1R,2S)-2-hydroxy-indan-1-ylamino)-quinolin-5-yl]-benzenesulfonamide;
   N5-(3H-Imidazol-4-ylmethyl)-N2-(R)-indan-1-yl-quinoline-2,5-diamine;
   N2-(R)-Indan-1-yl-N5-(3-methyl-3H-imidazol-4-ylmethyl)-quinoline-2,5-diamine;
   3,5-Difluoro-N-[2-((R)-indan-1-ylamino)-quinolin-5-yl]-benzamide;
   4-(Cyclopropylmethyl-amino)-N-[2-((R)-indan-1-ylamino)-quinolin-5-yl]-benzenesulfonamide;
   1-Methyl-1H-imidazole-4-sulfonic acid [2-((R)-indan-1-ylamino)-quinolin-5-yl]-amide;
   N5-(5-Fluoro-pyridin-3-yl)-N2-(R)-indan-1-yl-quinoline-2,5-diamine;
   N5-(1H-Imidazol-2-ylmethyl)-N2-(R)-indan-1-yl-quinoline-2,5-diamine;
   N2-(R)-Indan-1-yl-N5-(1H-pyrazol-3-ylmethyl)-quinoline-2,5-diamine;
   N-(2-Cyclohexylamino-quinolin-5-yl)-4-fluoro-benzenesulfonamide;
   3,5-Difluoro-N-[2-((1S,2R)-2-hydroxy-indan-1-ylamino)-quinolin-5-yl]-benzenesulfonamide;
   2-(R)-Indan-1-yl-N5-(2-methyl-1H-imidazol-4-ylmethyl)-quinoline-2,5-diamine;
   N-(2-Cycloheptylamino-quinolin-5-yl)-4-fluoro-benzenesulfonamide;
   N2-(R)-Indan-1-yl-N5-(1-methyl-1H-pyrazol-4-ylmethyl)-quinoline-2,5-diamine;
   N2-(R)-Indan-1-yl-N5-(1H-indol-4-ylmethyl)-quinoline-2,5-diamine;

rac-N5-(1H-Indol-4-ylmethyl)-N2-(7-methoxy-indan-1-yl)-quinoline-2,5-diamine;

N5-(1H-Imidazol-4-ylmethyl)-N2-(7-methoxy-indan-1-yl)-quinoline-2,5-diamine;

rac 3,5-Difluoro-N-[2-(8-methoxy-1,2,3,4-tetrahydro-naphthalen-1-ylamino)-quinolin-5-yl]-benzenesulfonamide;

and pharmaceutically-acceptable acid-addition salts thereof.

21. A pharmaceutical composition comprising a compound according to claim 1 and a pharmaceutically-acceptable excipient.

22. A process for the preparation of a compound according to claim 1 comprising reacting a compound of formula (a),

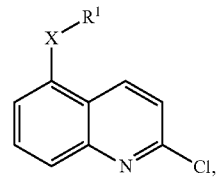

a with an amine of formula $R^2NH_2I$.